(12) United States Patent
Tsuruno

(10) Patent No.: US 10,945,707 B2
(45) Date of Patent: Mar. 16, 2021

(54) ULTRASONIC TRANSDUCER DEVICE, ULTRASONIC PROBE, AND ULTRASONIC APPARATUS

(71) Applicant: SEIKO EPSON CORPORATION, Tokyo (JP)

(72) Inventor: Jiro Tsuruno, Okaya (JP)

(73) Assignee: SEIKO EPSON CORPORATION, Tokyo (JP)

( * ) Notice: Subject to any disclaimer, the term of this patent is extended or adjusted under 35 U.S.C. 154(b) by 506 days.

(21) Appl. No.: 15/800,543

(22) Filed: Nov. 1, 2017

(65) Prior Publication Data

US 2018/0132824 A1    May 17, 2018

(30) Foreign Application Priority Data

Nov. 16, 2016  (JP) ................ JP2016-222948

(51) Int. Cl.
  *A61B 8/00* (2006.01)
  *B06B 1/06* (2006.01)
  *G01S 7/52* (2006.01)
  *G01S 15/89* (2006.01)

(52) U.S. Cl.
  CPC .......... *A61B 8/4483* (2013.01); *A61B 8/4444* (2013.01); *B06B 1/0607* (2013.01); *G01S 7/52079* (2013.01); *G01S 15/8925* (2013.01)

(58) Field of Classification Search
  CPC ... A61B 8/4444; A61B 8/4483; B06B 1/0607; G01S 15/8925; G01S 7/52079
  See application file for complete search history.

(56) References Cited

U.S. PATENT DOCUMENTS

| | | |
|---|---|---|
| 8,540,640 B2 | 9/2013 | Sano et al. |
| 9,082,394 B2 | 7/2015 | Matsuda et al. |
| 9,252,352 B2 | 2/2016 | Matsuda |
| 2010/0179430 A1 | 7/2010 | Sano et al. |
| 2012/0188849 A1 | 7/2012 | Matsuda et al. |
| 2014/0241113 A1 | 1/2014 | Matsuda |
| 2015/0092514 A1 | 4/2015 | Kiyose et al. |
| 2015/0288401 A1 | 10/2015 | Matsuda et al. |

FOREIGN PATENT DOCUMENTS

| | | |
|---|---|---|
| JP | 5049340 B2 | 10/2012 |
| JP | 5269307 B2 | 8/2013 |
| JP | 2014-161708 A | 9/2014 |
| JP | 2015-066203 A | 4/2015 |
| JP | 2015-177998 A | 10/2015 |
| WO | 2008-114582 A1 | 9/2008 |

*Primary Examiner* — Michael T Rozanski
(74) *Attorney, Agent, or Firm* — Oliff PLC

(57) ABSTRACT

An ultrasonic transducer device includes a first substrate that is provided with a plurality of ultrasonic transducer elements arranged in a matrix, and a plurality of first wires via which the ultrasonic transducer elements are electrically connected to each other as a plurality of serial sets, and a second substrate that is provided to overlap the first substrate, and is provided with a plurality of second wires intersecting the first wires in a plan view from a thickness direction of the first substrate and third wires via which the first wires are electrically connected to the second wires.

12 Claims, 13 Drawing Sheets

ULTRASONIC TRANSDUCER DEVICE, ULTRASONIC PROBE, AND ULTRASONIC APPARATUS

BACKGROUND

1. Technical Field

The present invention relates to an ultrasonic transducer device, an ultrasonic probe, and an ultrasonic apparatus.

2. Related Art

An ultrasonic apparatus is widely spread which transmits ultrasonic waves toward the inside of a subject, and generates an ultrasonic image by using ultrasonic waves reflected from the inside of the subject. The reflected ultrasonic waves are converted into an electrical signal in an ultrasonic transducer device. A lot of ultrasonic transducer elements are provided in the ultrasonic transducer device. The electrical signal output from the ultrasonic transducer device is a weak signal, and is amplified in an amplification circuit.

If an amplification factor of the amplification circuit is increased, a noise component is also amplified in addition to a signal component. If the noise component is increased, an ultrasonic image is unclear so as to be hardly viewed. Since an amplification factor of the amplification circuit can be lowered if an electrical signal output from the ultrasonic transducer device can be strengthened, the noise component can be reduced.

An "ultrasonic-guided central vein puncture method" using an ultrasonic apparatus for intravenous injection is performed. In this method, blood vessel running or the like is checked in an "ultrasonic image" before puncture. A puncture needle is caused to advance while checking a position, a direction, a depth, and the like of the puncture needle in the "ultrasonic image". It is checked whether or not the puncture needle reaches or is inserted into a vein. A catheter is inserted while confirming that a guide wire or the catheter is retained in the vein in the "ultrasonic image".

WO2008/114582 discloses an ultrasonic transducer device in which ultrasonic elements are disposed in a two-dimensional manner. According to the technique disclosed therein, an ultrasonic transducer element in which sensitivity is changed by changing a drive voltage applied between electrodes is used in the ultrasonic transducer device. A plurality of ultrasonic transducer elements are connected in parallel to each other so as to form an ultrasonic transducer element group.

An outer shape of the ultrasonic transducer device is a rectangular shape, and outputs electrical signals from four sides thereof. Consequently, even in a case where the number of ultrasonic transducer elements is large, wires for connection to a drive circuit are easily provided in the ultrasonic transducer device.

If terminals for providing wires connected to the ultrasonic transducer device are arranged on sides in different directions, wires for transmitting electrical signals are easily provided. Therefore, an apparatus in which wires for connection are arranged on sides in different directions is desirable. In the "ultrasonic-guided central vein puncture method", a relative position between a blood vessel and a needle tip is required to be received at a high resolution. In a case where ultrasonic elements are connected in parallel to each other, a plurality of ultrasonic elements receive ultrasonic waves, and thus the sensitivity can be increased. However, an ultrasonic transducer device which receives an ultrasonic wave with higher sensitivity is desirable in order to receive a relative position between a blood vessel and a needle tip.

SUMMARY

An advantage of some aspects of the invention is to solve at least a part of the problems described above, and the invention can be implemented as the following forms or application examples.

Application Example 1

An ultrasonic transducer device according to this application example includes a first substrate that is provided with a plurality of ultrasonic transducer elements arranged in a matrix, and a plurality of first wires via which the ultrasonic transducer elements are electrically connected to each other as a plurality of serial sets; and a second substrate that is provided to overlap the first substrate, and is provided with a plurality of second wires intersecting the first wires in a plan view from a thickness direction of the first substrate and third wires via which the first wires are electrically connected to the second wires.

According to this application example, the ultrasonic transducer device includes the first substrate and the second substrate. The first substrate and the second substrate are provided to overlap each other. A plurality of ultrasonic transducer elements are arranged in a matrix on the first substrate. The ultrasonic transducer elements are electrically connected in series to each other via the first wires, and the first wires are provided in a plurality.

A plurality of second wires and third wires are provided on the second substrate. The second wires intersect the first wires in a plan view from the thickness direction of the first substrate. The first wires and the second wires are electrically connected to each other via the third wires.

The ultrasonic transducer element receives an ultrasonic wave so as to output a voltage signal. The ultrasonic transducer element functions as an electric capacitor having a pair of electrodes, and electric charge is accumulated in each electrode when receiving the ultrasonic wave. The ultrasonic transducer elements are connected in series to each other, and thus electrostatic capacitance can be reduced. The electrostatic capacitance and the ultrasonic transducer device have an inverse proportion relationship. The ultrasonic transducer elements connected in series can output a change in electric charge in each electrode as a great voltage change by reducing the electrostatic capacitance.

In a case where ultrasonic transducer elements connected in series are set as a single ultrasonic transducer element unit, the ultrasonic transducer element unit has two terminals. One of the two terminals is referred to as the first terminal, and the other terminal is referred to as the second terminal. The first terminal is connected to the first wire, and signals are input and output via the first wire. An electrical signal output from the second terminal is output via the first wire, the third wire, and the second wire. Since a plurality of first wires and a plurality of second wires intersect each other, a direction in which the first wires are arranged and a direction in which the second wires are arranged are different directions. Therefore, electrical signals can be easily input and output between the first wire and the second wire, and the first terminal and the second terminal of each ultrasonic transducer element unit.

The first wire and the second wire are provided on the different substrates so as to be insulated from each other, and are thus connected to each other at only a specific location via the third wire. Therefore, it is also possible to prevent an electrical signal from leaking between the first wire and the second wire at a location where the first wire intersects the second wire. As a result, the ultrasonic transducer device can output electrical signals with high sensitivity, and thus the electrical signals can be transmitted from the wires arranged in different directions.

Application Example 2

In the ultrasonic transducer device according to the application example, the third wire includes through electrodes that penetrate through the second substrate and are connected to the second wires, and conductive protrusions via which the through electrodes are connected to the first wires.

According to this application example, the third wire includes the through electrode and the conductive protrusion. The through electrode penetrates through the second substrate so as to be connected to the second wire. The through electrode is connected to the first wire via the conductive protrusion. Therefore, the first wire and the second wire can be reliably connected to each other via the third wire.

Application Example 3

An ultrasonic transducer device according to this application example includes a substrate; a plurality of second wires that are provided on the substrate; an insulating film that is provided to overlap the second wires; a plurality of ultrasonic transducer elements that are provided on the insulating film and are arranged in a matrix; a plurality of first wires via which the ultrasonic transducer elements are electrically connected to each other as a plurality of serial sets and that intersect the second wires in a plan view from a thickness direction of the substrate; and third wires via which the first wires are electrically connected to the second wires.

According to this application example, the ultrasonic transducer device includes the substrate, and the second wires are provided on the substrate. An insulating film or the like may be disposed between the substrate and the second wires. The insulating film is provided to overlap the second wires. Other layers or films may be disposed between the second wires and the insulating film. For example, the second wires, an insulating film, a semiconductor layer, and the insulating film may be disposed. A plurality of ultrasonic transducer elements are provided on the insulating film, and the ultrasonic transducer elements are arranged in a matrix. The ultrasonic transducer elements are electrically connected to each other as a plurality of serial sets via the first wires. The second wires intersect the first wires in a plan view from the thickness direction of the substrate. The first wires and the second wires are provided in a plurality. The first wires and the second wires are electrically connected to each other via the third wires.

The ultrasonic transducer element receives an ultrasonic wave so as to output a voltage signal. The ultrasonic transducer element functions as an electric capacitor having a pair of electrodes, and electric charge is accumulated in each electrode when receiving the ultrasonic wave. The ultrasonic transducer elements are connected in series to each other, and thus electrostatic capacitance can be reduced. The electrostatic capacitance and the ultrasonic transducer device have an inverse proportion relationship. The ultrasonic transducer elements connected in series can output a change in electric charge in each electrode as a great voltage change by reducing the electrostatic capacitance.

In a case where ultrasonic transducer elements connected in series are set as a single ultrasonic transducer element unit, the ultrasonic transducer element unit has two terminals. One of the two terminals is referred to as the first terminal, and the other terminal is referred to as the second terminal. The first terminal is connected to the first wire, and signals are input and output via the first wire. An electrical signal output from the second terminal is output via the first wire, the third wire, and the second wire. Since a plurality of first wires and a plurality of second wires intersect each other, a direction in which the first wires are arranged and a direction in which the second wires are arranged are different directions. Therefore, electrical signals can be easily input and output between the first wire and the second wire, and the first terminal and the second terminal of each ultrasonic transducer element unit.

The first wire and the second wire are provided with the insulating film interposed therebetween so as to be insulated from each other, and are thus connected to each other at only a specific location via the third wire. Therefore, it is also possible to prevent an electrical signal from leaking between the first wire and the second wire at a location where the first wire intersects the second wire. As a result, the ultrasonic transducer device can output electrical signals with high sensitivity, and thus the electrical signals can be transmitted from the wires arranged in different directions.

Application Example 4

In the ultrasonic transducer device according to the application example, the number of ultrasonic transducer elements electrically connected as the serial sets is two or more and five or less.

According to this application example, the number of ultrasonic transducer elements electrically connected as serial sets is two or more and five or less. If two or more ultrasonic transducer elements are provided, the ultrasonic transducer elements can be connected in series to each other. Waveforms of ultrasonic waves received by the respective ultrasonic transducer elements are different from each other due to the influence of a subject.

If six or more ultrasonic transducer elements are connected in series to each other, the sensitivity of the ultrasonic transducer element unit is saturated due to the influence of a difference between ultrasonic waves received by the respective ultrasonic transducer elements. Therefore, if the number of ultrasonic transducer elements is five or less, the sensitivity of the ultrasonic transducer device can be efficiently made favorable.

In a case where six or more ultrasonic transducer elements are connected in series to each other, a voltage applied to the ultrasonic transducer element unit is heightened. A breakdown voltage of a drive circuit for driving the ultrasonic transducer element unit is required to be heightened, and thus it is difficult to obtain an element forming the drive circuit. Therefore, if the number of ultrasonic transducer elements is five or less, a breakdown voltage of the drive circuit can be lowered, and thus it is possible to easily manufacture the drive circuit.

Application Example 5

An ultrasonic transducer device according to this application example includes an ultrasonic transducer element group in which ultrasonic transducer element units each including a plurality of ultrasonic transducer elements connected in series are arranged in a matrix; a first wire that is connected to a first terminal of each of the ultrasonic transducer element unit and extends in a first direction; and a second wire that is connected to a second terminal of each of the ultrasonic transducer element unit and extends in a second direction, in which the first wire and the second wire are separated from and intersect each other.

According to this application example, the ultrasonic transducer device includes the ultrasonic transducer element group. The ultrasonic transducer element group includes the ultrasonic transducer element units each including a plurality of ultrasonic transducer elements connected in series, and the ultrasonic transducer element units are arranged in a matrix. The ultrasonic transducer element is a two-terminal element, and the ultrasonic transducer element unit in which the ultrasonic transducer elements are connected in series to each other is a two-terminal unit. One of two terminals is the first terminal, and the other terminal is the second terminal. The first terminal is connected to the first wire, and the first wire extends in the first direction. The second terminal is connected to the second wire, and the second wire extends in the second direction. The ultrasonic transducer element units are arranged in a matrix, and a plurality of first wires and second wires are provided. The first wires and the second wires intersect each other, and thus a direction in which the first wires are arranged and a direction in which the second wires are arranged are different from each other.

The ultrasonic transducer element receives an ultrasonic wave so as to output a voltage signal. The ultrasonic transducer element functions as an electric capacitor having a pair of electrodes, and electric charge is accumulated in each electrode when receiving the ultrasonic wave. The ultrasonic transducer elements are connected in series to each other, and thus electrostatic capacitance can be reduced. The electrostatic capacitance and a voltage output from the ultrasonic transducer element have an inverse proportion relationship. The ultrasonic transducer elements connected in series can output a change in electric charge in each electrode as a great voltage change by reducing the electrostatic capacitance.

The ultrasonic transducer element unit has the first terminal and the second terminal. The first terminal is connected to the first wire, and signals are input and output via the first wire. The second terminal is connected to the second wire, and signals are input and output via the second wire. A direction in which the first wires are arranged and a direction in which the second wires are arranged are different directions. Therefore, electrical signals can be easily input and output between the first wire and the second wire, and the first terminal and the second terminal of each ultrasonic transducer element unit, compared with a case where the first wires and the second wires are arranged in the same direction. As a result, the ultrasonic transducer device can output electrical signals with high sensitivity, and thus the electrical signals can be transmitted from the wires arranged in different directions.

Application Example 6

An ultrasonic probe according to this application example includes an ultrasonic transducer device that receives an ultrasonic wave and outputs an electrical signal, in which the ultrasonic transducer device is any one of the above ultrasonic transducer devices.

According to this application example, the ultrasonic probe includes the ultrasonic transducer device which receives an ultrasonic wave and outputs an electrical signal. The ultrasonic transducer device is the above-described ultrasonic transducer device. The above-described ultrasonic transducer device can output electrical signals with high sensitivity, and thus the electrical signals can be transmitted from the wires arranged in different directions. Therefore, the ultrasonic probe can acquire the signals with high sensitivity, and can thus be implemented as a device including the ultrasonic transducer device which can transmit electrical signals from the wires arranged in different directions.

Application Example 7

An ultrasonic apparatus according to this application example includes an ultrasonic transducer device that receives an ultrasonic wave and outputs an electrical signal; a converter that converts the electrical signal output from the ultrasonic transducer device into a data signal; and a display that displays the data signal, in which the ultrasonic transducer device is any one of the above ultrasonic transducer devices.

According to this application example, the ultrasonic apparatus includes the ultrasonic transducer device, the converter, and the display. The ultrasonic transducer device receives an ultrasonic wave and outputs an electrical signal. The converter converts the electrical signal into a data signal. The display displays the data signal. The above-described ultrasonic transducer device is used as the ultrasonic transducer device. The above-described ultrasonic transducer device can output electrical signals with high sensitivity, and thus the electrical signals can be transmitted from the wires arranged in different directions. Therefore, the ultrasonic apparatus can output electrical signals with high sensitivity, and can thus be implemented as an apparatus including the ultrasonic transducer device which can transmit the electrical signals from the wires arranged in different directions.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments will be described with reference to the drawings.

In the following diagrams, a scale of each member differs since each member is exaggerated to be able to be recognized.

First Embodiment

In the present embodiment, a description will be made of characteristic examples of an ultrasonic transducer device and a manufacturing method of the ultrasonic transducer device with reference to the drawings. An ultrasonic transducer device according to the first embodiment will be described with reference to FIGS. 1 to 23.

Figure 1:
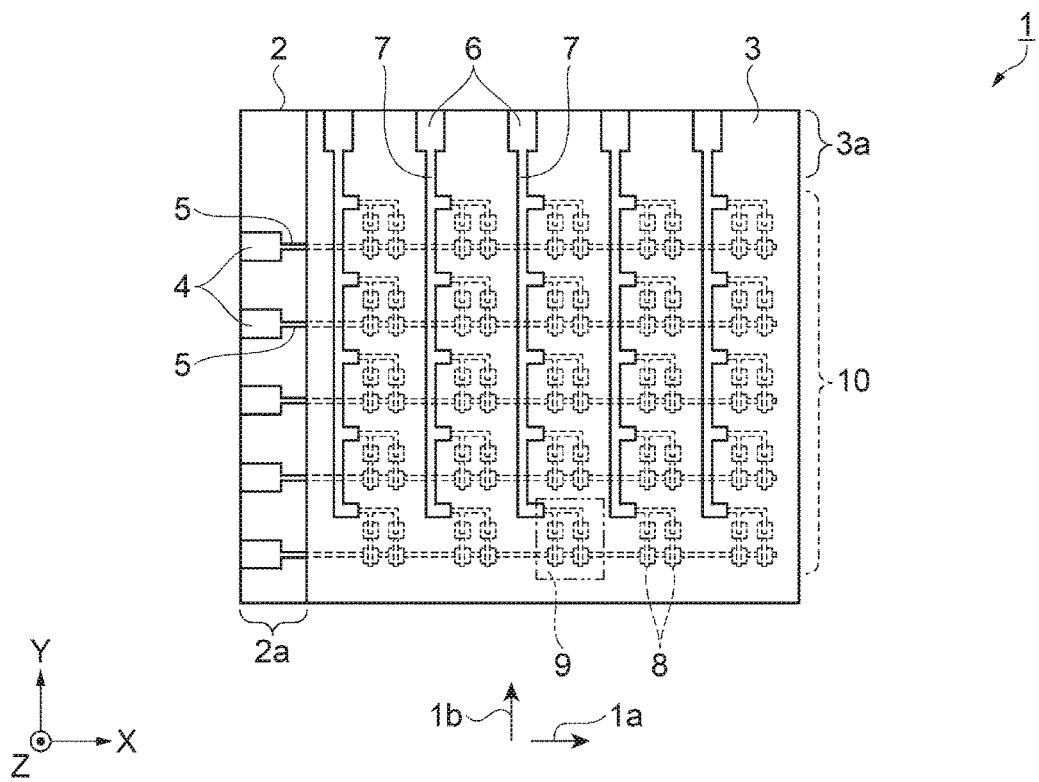
FIG. 1 is a schematic plan view illustrating a structure of an ultrasonic transducer device according to a first embodiment.

FIG. 1 is a schematic plan view illustrating a structure of an ultrasonic transducer device. As illustrated in FIG. 1, an ultrasonic transducer device 1 includes a first substrate 2 and a second substrate 3. The second substrate 3 overlaps the first substrate 2.

The first substrate 2 has a rectangular shape, and two sides adjacent to each other are orthogonal to each other. A direction in which a certain side extends is set to an X direction, and a direction in which one side adjacent to the side in the X direction extends is set to a Y direction. A thickness direction of the first substrate 2 is set to a Z direction.

Lengths of the first substrate 2 and the second substrate 3 in the Y direction are the same as each other. The first substrate 2 is longer than the second substrate 3 in the X direction, and there is a structure in which the first substrate 2 is viewed to be exposed on the −X direction side of the second substrate 3 when viewed from the +Z direction side. The exposed portion in the first substrate 2 is referred to as a first terminal region 2a.

First external terminals 4 are provided to be arranged in the Y direction in the first terminal region 2a. First wires 5 extending in the +X direction are connected to the first external terminals 4. A location close to an end of the second substrate 3 on the +Y direction side is referred to as a second terminal region 3a. Second external terminals 6 are provided to be arranged in the X direction in the second terminal region 3a. Second wires 7 extending in the −Y direction are connected to the second external terminals 6.

A direction in which the first wire 5 extends is set to a first direction 1a, and a direction in which the second wire 7 extends is set to a second direction 1b. The first direction 1a and the second direction 1b are orthogonal to each other.

A plurality of ultrasonic elements 8 arranged in a matrix as ultrasonic transducer elements are provided on the first substrate 2. The number of rows and the number of columns of the ultrasonic elements 8 are not particularly limited. In the present embodiment, for example, the ultrasonic transducer device 1 is provided with the ultrasonic elements 8 of ten rows and ten columns.

An ultrasonic element unit 9 as a single ultrasonic transducer element unit is formed of the ultrasonic elements 8 of two rows and two columns. Therefore, the single ultrasonic element unit 9 includes four ultrasonic elements 8. The ultrasonic element units 9 are arranged in a matrix so as to form an ultrasonic element group 10 as an ultrasonic transducer element group. The number of rows and the number of columns of the ultrasonic element units 9 are not particularly limited. In the present embodiment, for example, the single ultrasonic element group 10 is formed of the ultrasonic element units 9 of five rows and five columns.

Figure 2:
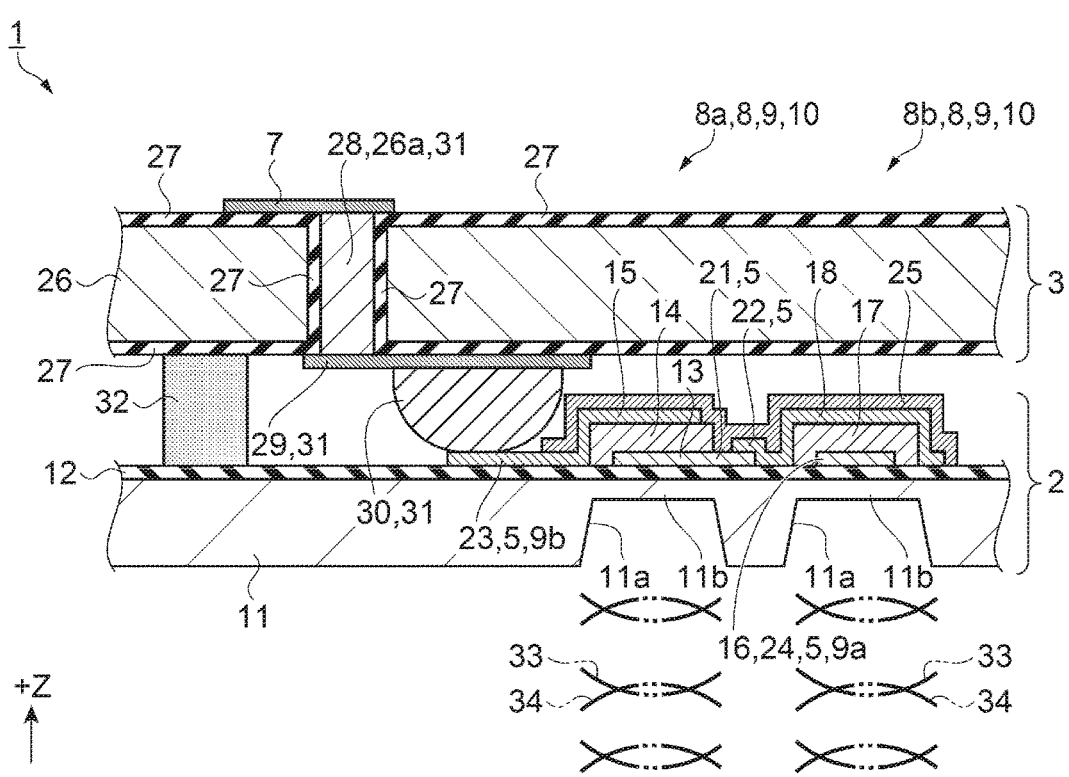
FIG. 2 is a main portion schematic side sectional view illustrating a configuration of the ultrasonic transducer device.

FIG. 2 is a main portion schematic side sectional view illustrating a configuration of the ultrasonic transducer device. As illustrated in FIG. 2, the ultrasonic elements 8 forming the ultrasonic element unit 9 are provided to be arranged on the first substrate 2. The ultrasonic element 8 on the left in the figure is referred to as a first element 8a, and the ultrasonic element 8 on the right in the figure is referred to as a second element 8b.

The first substrate 2 includes a first base plate 11. The first base plate 11 is provided with a depression 11a at a location opposing the ultrasonic element 8. A thickness of the first base plate 11 is thinned in the depression 11a, and thus the thin portion is a vibration plate 11b which easily vibrates.

A material of the first base plate 11 is not particularly limited, and may have the strength and may be subjected to fine processing. In the present embodiment, for example, a silicon substrate is used as the first base plate 11. A material of the vibration plate 11b is not particularly limited as long as the material has a favorable vibration characteristic. The vibration plate 11b preferably has insulating property. In the present embodiment, for example, silicon dioxide or zirconium dioxide is used as a material of the vibration plate 11b.

An insulating film 12 is provided on the first base plate 11 on the +Z direction side. In a case where the vibration plate 11b has insulating property, and a material of the vibration plate 11b covers a surface of the first base plate 11 on the +Z direction side, the vibration plate 11b may also be used as the insulating film 12. Silicon dioxide or aluminum dioxide may be used as a material of the insulating film 12.

A first lower electrode 13, a piezoelectric body 14, and a first upper electrode 15 are provided to overlap each other on the insulating film 12. The first element 8a is formed of the vibration plate 11b, the first lower electrode 13, the piezoelectric body 14, and the first upper electrode 15. A second lower electrode 16, a piezoelectric body 17, and a second upper electrode 18 are provided to overlap each other on the insulating film 12. The second element 8b is formed of the vibration plate 11b, the second lower electrode 16, the piezoelectric body 17, and the second upper electrode 18.

A first connection wire 21 which is connected to the first lower electrode 13 and is directed toward the second element 8b from the first lower electrode 13 is provided on the insulating film 12. A second connection wire 22 is provided toward the first element 8a from the second upper electrode 18. The first connection wire 21 and the second connection wire 22 are connected to each other. Therefore, the first lower electrode 13 is electrically connected to the second upper electrode 18.

The first upper electrode 15 is connected to a third connection wire 23, and the third connection wire 23 extends to the left in the figure on the insulating film 12. The second lower electrode 16 is connected to a fourth connection wire 24, and the fourth connection wire 24 extends in the X direction so as to be connected to the first external terminal 4.

The fourth connection wire 24 serves as a first terminal 9a in the ultrasonic element unit 9. The third connection wire 23 serves as a second terminal 9b in the ultrasonic element unit 9. The first element 8a and the second element 8b are connected in series to each other in the ultrasonic element unit 9.

A protective film 25 is provided on the insulating film 12 so as to cover the first element 8a, the second element 8b, the fourth connection wire 24, and a part of the third connection wire 23. The protective film 25 prevents moisture from entering the piezoelectric body 14 and the piezoelectric body 17, and prevents leakage between wires due to dust. The protective film 25 may be formed as an insulating film by using an inorganic substance such as silicon oxide or aluminum oxide as a material thereof. In the present embodiment, for example, aluminum oxide is used as a material of an inorganic insulating film which is the protective film 25. The protective film 25 may have a configuration in which a resin film is provided to overlap the inorganic insulating film.

The type of piezoelectric body 14 and the piezoelectric body 17 is not particularly limited, but a piezoelectric body such as a lead zirconate titanate (PZT) element or a polyvinylidene fluoride (PDVF) element may be used. In the present embodiment, the PZT element is used as the piezoelectric body 14 and the piezoelectric body 17.

Materials of the first lower electrode 13, the first upper electrode 15, the second lower electrode 16, the second upper electrode 18, the first connection wire 21, the second connection wire 22, the third connection wire 23, and the fourth connection wire 24 may be conductive and stable, and, in the present embodiment, for example, a film in which an iridium film and a platinum film are laminated is used.

The second substrate 3 includes a second base plate 26. An insulating film 27 is provided on both surfaces such as a surface of the second base plate 26 on the +Z direction side and a surface thereof on the −Z direction side. The same material as in the insulating film 12 is used for the insulating film 27.

A through hole 26a which penetrates in the thickness direction is provided in the second base plate 26. The inside of the through hole 26a is covered with the insulating film 27. A through electrode 28 in which a metal is embedded in the inside of the through hole 26a is provided in the second base plate 26.

A fifth connection wire 29 is provided on the surface of the second substrate 3 facing the first substrate 2, and the fifth connection wire 29 is connected to the through electrode 28. The fifth connection wire 29 is provided with a conductive protrusion 30. The protrusion 30 protrudes from the fifth connection wire 29 toward the third connection wire 23, and thus the protrusion 30 is connected to the third connection wire 23. The third connection wire 23 is a part of the first wire 5. A third wire 31 is formed of the through electrode 28, the fifth connection wire 29, and the protrusion 30.

The second substrate 3 is provided with the second wire 7 and the third wire 31, and the first wire 5 and the second wire 7 are electrically connected to each other via the third wire 31.

The second wire 7 is provided on the surface of the second substrate 3 on the Z direction side, and the second wire 7 is connected to the through electrode 28. Therefore, the third wire 31 includes the through electrode 28 which penetrates through the second substrate 3 so as to be connected to the second wire 7, and the conductive protrusion 30 via which the through electrode 28 is electrically connected to the first wire 5.

The first substrate 2 and the second substrate 3 are provided to overlap each other. An adhesive portion 32 is provided at a plurality of locations between the first substrate 2 and the second substrate 3. The adhesive portion 32 adheres the first substrate 2 to the second substrate 3. The adhesive portion 32 has tension of attracting the first substrate 2 and the second substrate 3. Consequently, the protrusion 30 is pressed against the third connection wire 23, and thus the protrusion 30 and the third connection wire 23 can be reliably electrically connected to each other.

Materials of the through electrode 28 and the protrusion 30 are not particularly limited as long as the materials are conductive. In the present embodiment, for example, a metal such as copper or aluminum may be used as a material of the through electrode 28, and a metal such as a tin alloy or copper may be used as a material of the protrusion 30.

The ultrasonic element 8 emits an ultrasonic wave 33 toward the −Z direction side. A reflected wave 34 as an ultrasonic wave reflected in a subject is received. A voltage with a drive waveform is applied between the first terminal 9a and the second terminal 9b, and thus the first element 8a and the second element 8b vibrate to emit the ultrasonic waves 33. When the reflected waves 34 reach the ultrasonic element 8, the first element 8a and the second element 8b vibrate, and thus a voltage waveform corresponding to the reflected waves 34 is output between the first terminal 9a and the second terminal 9b.

The first terminal 9a is connected to the first external terminal 4 via the fourth connection wire 24. The second terminal 9b is connected to the second external terminal 6 via the second wire 7. Therefore, a drive waveform is input between the first external terminal 4 and the second external terminal 6, and thus the ultrasonic element 8 can be driven. A voltage waveform corresponding to the reflected waves 34 can be output from between the first external terminal 4 and the second external terminal 6.

Figure 3:
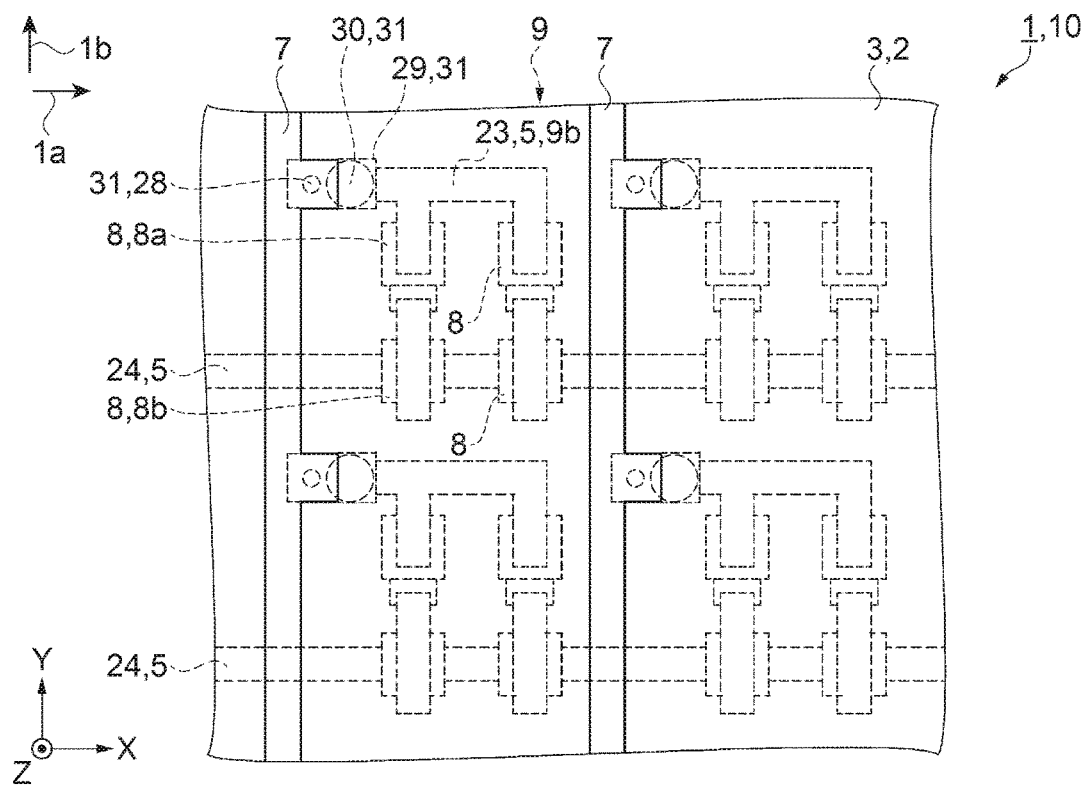
FIG. 3 is a main portion schematic plan view illustrating a structure of the ultrasonic transducer device.

FIG. 3 is a main portion schematic plan view illustrating a structure of the ultrasonic transducer device, and is a view in which the ultrasonic transducer device 1 is viewed from the +Z direction side. As illustrated in FIG. 3, a plurality of second wires 7 are provided to extend in the Y direction on the second substrate 3 on the +Z side.

Four ultrasonic elements 8 are provided in a single ultrasonic element unit 9. The through electrode 28 connected to the second wire 7 is provided in each ultrasonic element unit 9. The second wire 7 is electrically connected to the ultrasonic element unit 9 via the through electrode 28, the fifth connection wire 29, the protrusion 30, and the third connection wire 23. A plurality of second wires intersect the first wires 5 in a plan view from the thickness direction of the first substrate 2. The third connection wire 23 which is the second terminal 9b is connected to the second wire 7 extending in the second direction 1b.

Figure 4:
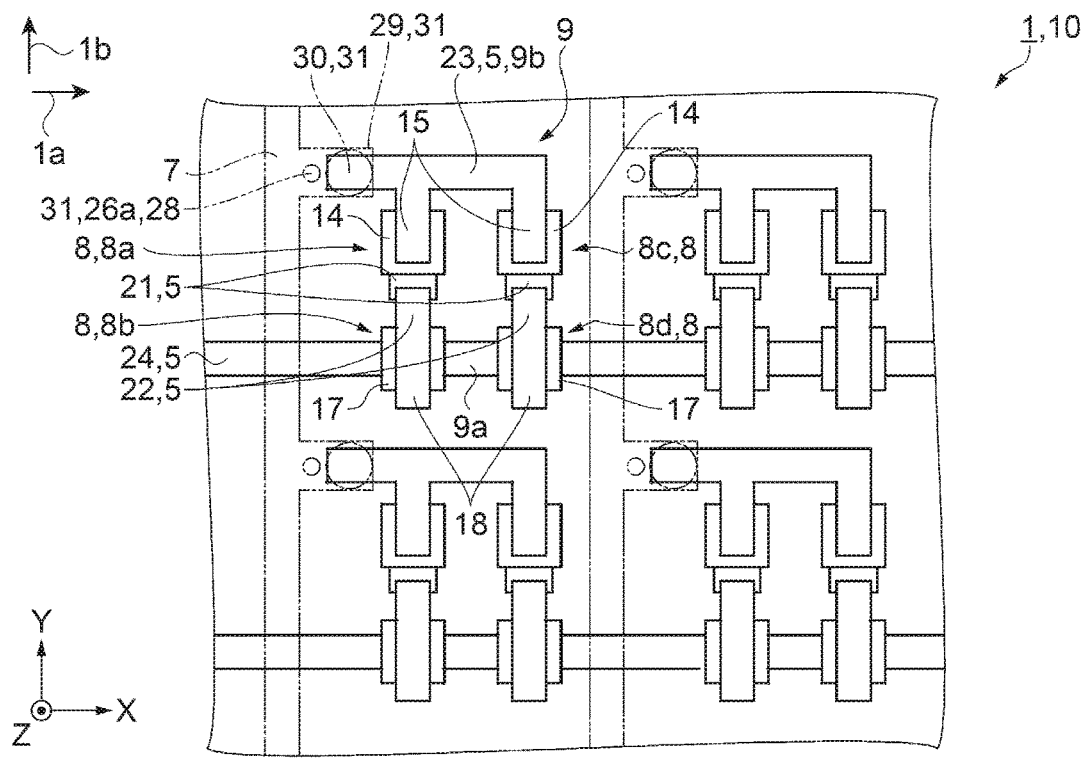
FIG. 4 is a main portion schematic plan view illustrating a structure of the ultrasonic transducer device.

FIG. 4 is a main portion schematic plan view illustrating a structure of the ultrasonic transducer device, and is a view in which the first substrate 2 is viewed from the +Z direction side. In FIG. 4, the protective film 25 is not illustrated. As illustrated in FIG. 4, a plurality of ultrasonic elements 8 arranged in a matrix are provided on the first substrate 2. The ultrasonic element unit 9 is formed of the first element 8a, the second element 8b, a third element 8c, and a fourth element 8d.

The first wire 5 is formed of the fourth connection wire 24, the first upper electrode 15, the first connection wire 21, and the third connection wire 23, and the first element 8a and the second element 8b are connected in series to each other via the first wire 5. The third element 8c is provided on the +X direction side of the first element 8a, and the fourth element 8d is provided on the +X direction side of the second element 8b.

The third element 8c and the fourth element 8d are connected in series to each other via the first wire 5. The first element 8a and the second element 8b connected in series and the third element 8c and the fourth element 8d connected in series are connected in parallel to each other via the third connection wire 23 and the fourth connection wire 24. In other words, the ultrasonic elements 8 are electrically connected to each other as a plurality of serial sets via the first wire 5. The ultrasonic elements 8 and the first wires 5 are provided on the first substrate 2.

In the ultrasonic element unit 9, a plurality of ultrasonic elements 8 are connected in series to each other. In the ultrasonic element group 10, the ultrasonic element units 9 are arranged in a matrix. The ultrasonic element unit 9 has the first terminal 9a and the second terminal 9b. The first terminal 9a is connected to the first wire 5 extending in the first direction 1a. The second terminal 9b is connected to the second wire 7 extending in the second direction 1b. The first wire 5 and the second wire 7 are separated from each other in the Z direction, and intersect each other in a plan view which is viewed from the Z direction. In other words, the first wire 5 and the second wire 7 are separated from and intersect each other.

Figure 5:
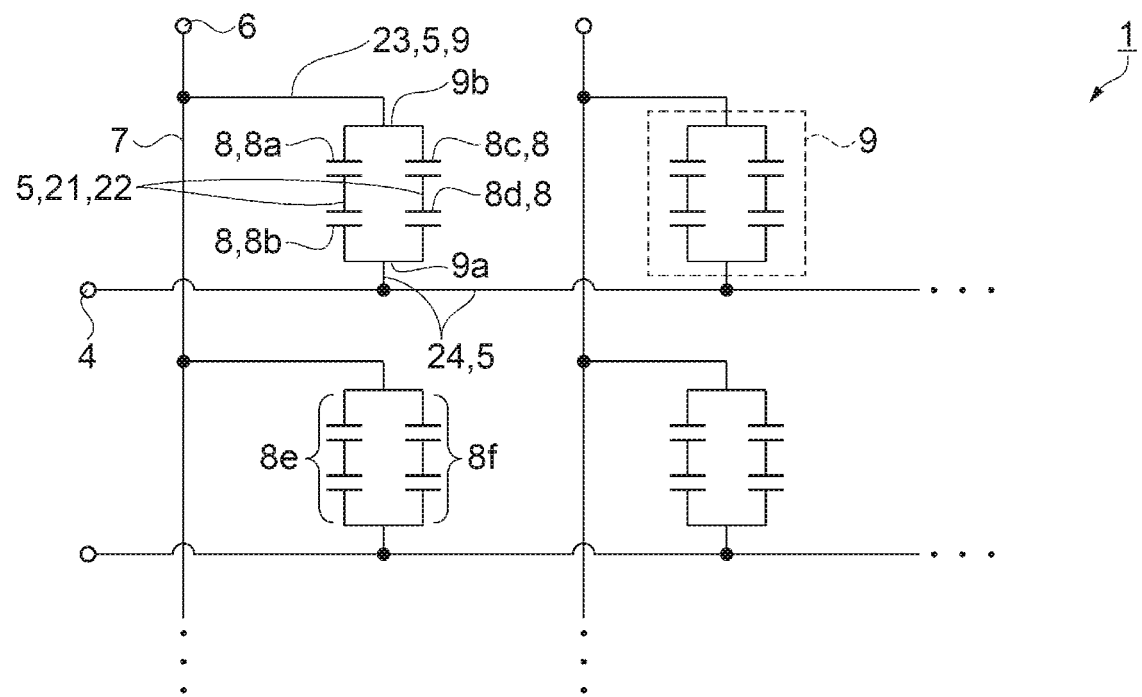
FIG. 5 is an electric circuit diagram of the ultrasonic transducer device.

FIG. 5 is an electrical circuit diagram of the ultrasonic transducer device. As illustrated in FIG. 5, in the ultrasonic transducer device 1, the ultrasonic element units 9 are arranged in a matrix. In each ultrasonic element unit 9, the first element 8a and the second element 8b are connected in series to each other, and the third element 8c and the fourth element 8d are connected in series to each other.

A circuit in which the first element 8a and the second element 8b are connected in series to each other is referred to as a first element circuit 8e. A circuit in which the third element 8c and the fourth element 8d are connected in series to each other is referred to as a second element circuit 8f. The first element circuit 8e and the second element circuit 8f are connected in parallel to each other. In other words, the ultrasonic elements 8 are electrically connected to each other as a plurality of serial sets via the first wire 5.

Figure 6:
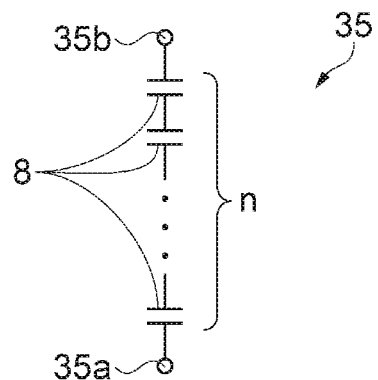
FIG. 6 is a circuit diagram for explaining an element circuit.

FIG. 6 is a circuit diagram for explaining the element circuit. In each of the first element circuit 8e and the second element circuit 8f, two ultrasonic elements 8 are connected in series to each other. As illustrated in FIG. 6, an element circuit 35 in which a plurality of ultrasonic elements 8 are connected in series to each other may be used. In the element circuit 35, n ultrasonic elements 8 are connected in series to each other between a first terminal 35a and a second terminal 35b.

Figure 7:
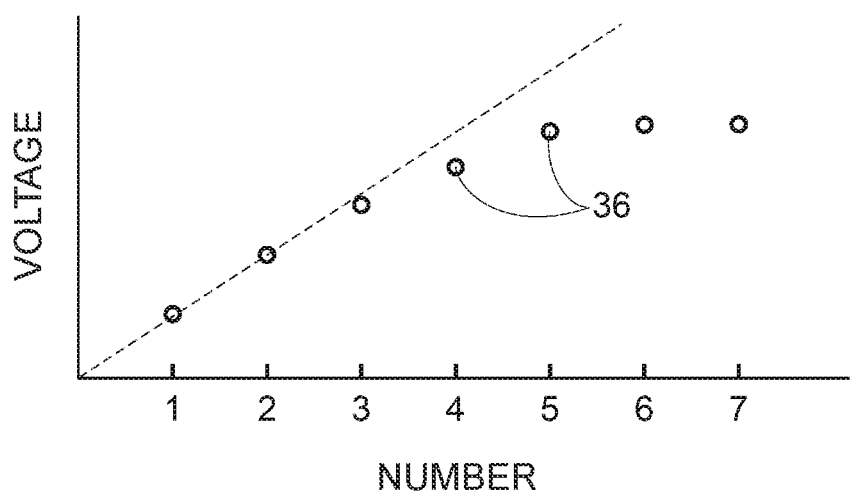
FIG. 7 is a diagram for explaining a relationship between the number of ultrasonic elements and an output voltage in the element circuit.

FIG. 7 is a diagram for explaining a relationship between the number of ultrasonic elements and an output voltage in the element circuit. In FIG. 7, a transverse axis expresses the number of ultrasonic elements 8 in the element circuit 35. A longitudinal axis expresses a voltage output from between the first terminal 35a and the second terminal 35b when the constant ultrasonic wave 33 is emitted toward the element circuit 35. The ultrasonic wave 33 is a sine wave, and the voltage expressed on the longitudinal axis indicates an effective voltage of an AC voltage waveform.

The ultrasonic wave 33 is emitted from a point sound source which is far away from the element circuit 35 by a predetermined distance. Each plot 36 indicates an output voltage for the number of ultrasonic elements 8 in the element circuit 35 when the element circuit 35 receives the ultrasonic wave 33. As indicated by the plots 36, an output voltage also increases if the number of ultrasonic elements 8 connected in series increases up to one to five. An output voltage does not increases if the number of ultrasonic elements 8 connected in series is six or more.

The reason may be as follows. In a case where each ultrasonic element 8 is far away from a point sound source, the ultrasonic waves 33 with the same phase reach the respective ultrasonic elements 8, and thus an output voltage can be increased as the number of ultrasonic elements 8 is increased. In a case where each ultrasonic element 8 is close to the point sound source, phases of the ultrasonic waves 33 reaching the respective ultrasonic elements 8 are different from each other, and thus a combination of great phase differences occurs as the number of ultrasonic elements 8 is increased. In this case, even if the ultrasonic elements 8 are connected in series to each other, a voltage is not increased due to the influence of the phase difference between the ultrasonic waves 33 received by the respective ultrasonic elements 8.

Therefore, the number of ultrasonic elements 8 electrically connected in series is preferably two or more and five or less. In a case where two or more ultrasonic elements 8 are connected in series to each other, waveforms of the ultrasonic waves 33 received by the ultrasonic elements 8 are influenced by a subject and are thus different waveforms. If six or more ultrasonic elements 8 are connected in series to each other, the sensitivity of the ultrasonic element unit 9 is saturated due to the influence of a difference between waveforms received by the respective ultrasonic elements 8. Therefore, if the number of ultrasonic elements 8 is five or less, the sensitivity of the ultrasonic transducer device 1 can be efficiently made favorable.

When the ultrasonic element 8 receives the reflected wave 34 so as to output a voltage waveform, a predetermined voltage is applied to the piezoelectric body 14 and the piezoelectric body 17 in each ultrasonic element 8. In this case, a voltage change corresponding to the reflected wave 34 is added to a predetermined voltage in the ultrasonic element 8. In a case where six or more ultrasonic elements 8 are connected in series to each other, a voltage applied to the ultrasonic element unit 9 is heightened. As the number of ultrasonic elements 8 connected in series is increased, a breakdown voltage of a drive circuit for driving the ultrasonic element unit 9 is required to be heightened. It is difficult to obtain an element forming the drive circuit. Therefore, if the number of ultrasonic elements 8 is five or less, a breakdown voltage of the drive circuit can be lowered, and thus it is possible to easily manufacture the drive circuit.

Figure 8:
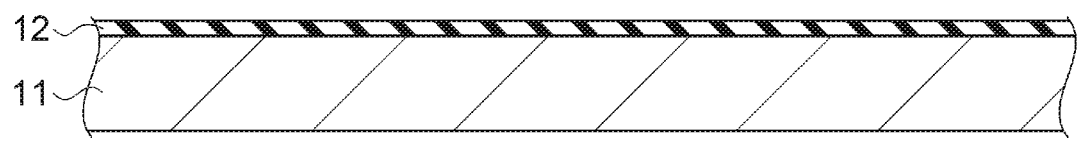
FIG. 8 is a schematic diagram for explaining a manufacturing method of the ultrasonic transducer device.

FIGS. 8 to 23 are schematic diagrams for explaining a manufacturing method of the ultrasonic transducer device. Next, with reference to FIGS. 8 to 23, a description will be made of a manufacturing method of the ultrasonic transducer device 1. FIG. 8 is a schematic diagram for explaining a vibration plate installation process. As illustrated in FIG. 8, the first base plate 11 is prepared. A layer which serving as the vibration plate 11b is provided on the first base plate 11. First, a silicon oxide layer ($SiO_2$) is laminated on a surface of the first base plate 11, and a zirconium oxide layer ($ZrO_2$) is laminated on a surface of the silicon oxide layer. A sputtering method or a chemical vapor deposition (CVD) method may be used as a method of laminating materials.

The insulating film 12 is provided on the vibration plate. The insulating film 12 is formed by laminating silicon dioxide or aluminum oxide. A sputtering method or a CVD method may be used as a method of laminating a material of the insulating film 12.

Figure 9:
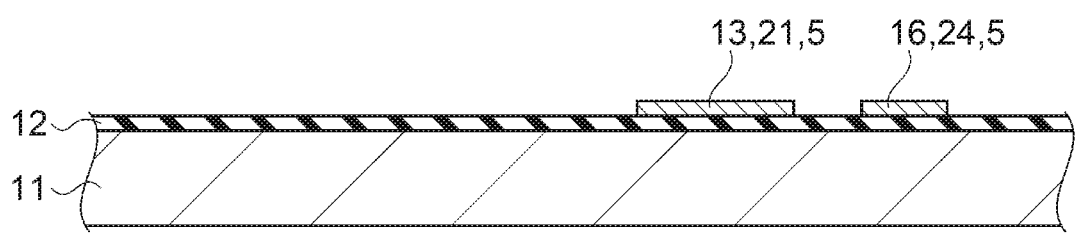
FIG. 9 is a schematic diagram for explaining a manufacturing method of the ultrasonic transducer device.

FIG. 9 is a schematic diagram for explaining a lower electrode installation process. As illustrated in FIG. 9, the first lower electrode 13, the second lower electrode 16, the first connection wire 21, and the fourth connection wire 24 are provided on the insulating film 12. First, a metal film is provided on the insulating film 12. In the present embodiment, for example, the metal film is a layer in which platinum is laminated on iridium oxide. A method of providing a metal film is not particularly limited, but, in the present embodiment, for example, a sputtering method is used.

Next, a photosensitive resist is provided on the metal film, and a mask having shapes of the first lower electrode 13, the second lower electrode 16, the first connection wire 21, and the fourth connection wire 24 is overlapped thereon so as to be exposed to light. Next, the photosensitive resist is removed through etching, and the metal film is etched by using the resist as a mask, and then the resist is removed. As a result, the first lower electrode 13, the second lower electrode 16, the first connection wire 21, and the fourth connection wire 24 are provided on the insulating film 12.

Figure 10:
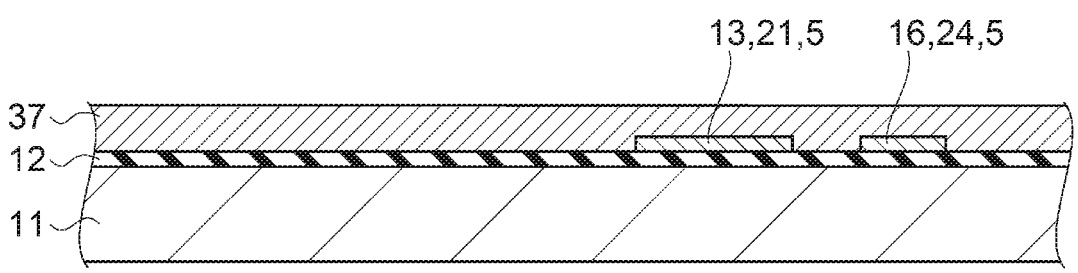
FIG. 10 is a schematic diagram for explaining a manufacturing method of the ultrasonic transducer device.
Figure 11:
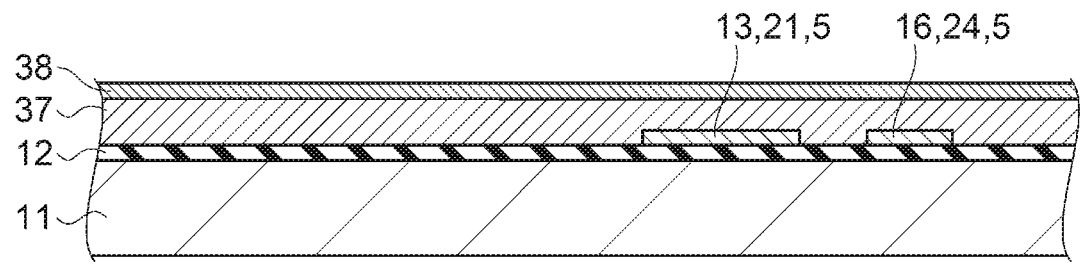
FIG. 11 is a schematic diagram for explaining a manufacturing method of the ultrasonic transducer device.
Figure 12:
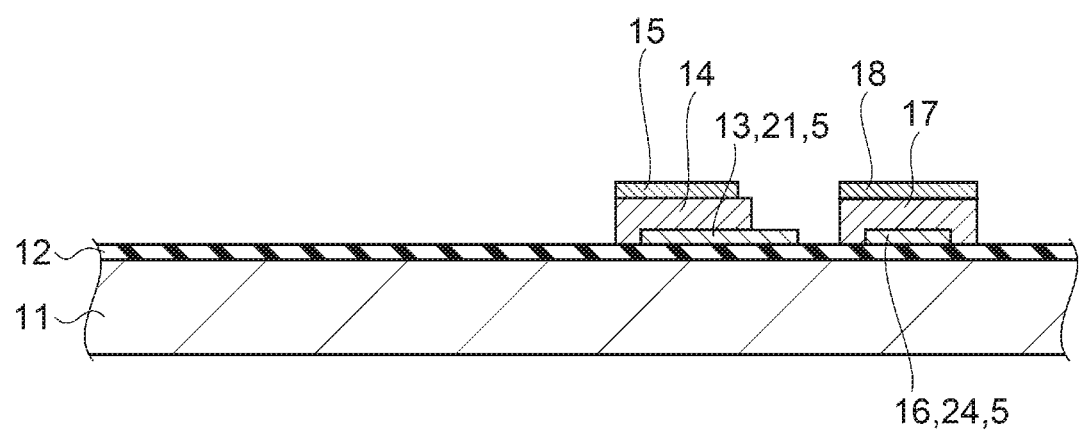
FIG. 12 is a schematic diagram for explaining a manufacturing method of the ultrasonic transducer device.

FIGS. 10 to 12 are schematic diagrams for explaining a piezoelectric body installation process. As illustrated in FIG. 10, a pyroelectric body material layer 37 is provided. The pyroelectric body material layer 37 is a layer serving as a material of the piezoelectric body 14 and the piezoelectric body 17, and is a PZT film layer. The pyroelectric body material layer 37 is provided by using a sputtering method or a sol-gel method. In the sputtering method, an amorphous piezoelectric body film precursor film is formed on the insulating film 12 through sputtering by using a PZT sintered body with a specific component as a sputtering target.

Next, the amorphous piezoelectric body film precursor film is heated to be crystallized, and is thus sintered. This heating is performed in an oxygen atmosphere such as oxygen or a mixed gas containing oxygen and an inert gas such as argon. In the heating process, the piezoelectric body film precursor film is heated at a temperature of 500° C. to 700° C. in the oxygen atmosphere. The piezoelectric body film precursor film is crystallized through heating.

In the sol-gel method, a sol which is a hydrate complex of a hydroxide of titanium, zirconium, lead, or the like which is a material of the pyroelectric body material layer 37 is prepared. This sol is dehydrated so that a gel is formed. This gel is heated and baked to prepare the pyroelectric body material layer 37 which is an inorganic oxide. A starting material is alkoxide or acetate of each of titanium, zirconium, lead, and other metal components. The sol is a starting material. The sol is used as a composition mixed with an organic polymer compound. The organic polymer compound absorbs remaining stress of the pyroelectric body material layer 37 during drying and baking, and thus reduces concern that a crack may occur in the pyroelectric body material layer 37.

Next, the sol composition is coated on the insulating film 12. Various coating methods or a printing method is used as a coating method. After coating, a film of the sol composition is dried. Drying may be natural drying, or may be performed through heating at a temperature of 80° C. or higher and 200° C. or lower. Next, the film of the sol composition is baked. The baking is performed for about 10 to 120 minutes in a range of a baking temperature of 300° C. to 450° C. The film of the sol composition is gelled through the baking.

Next, baking is performed again after changing a temperature. The baking is performed for about 0.1 to 5 hours in a range of a baking temperature of 400° C. to 800° C. In the re-baking, a first stage is performed at a temperature in a range of 400° C. to 600° C. Next, a second stage is performed at a temperature in a range of 600° C. to 800° C. or lower. Consequently, a porous gel thin film is converted into a film made of a crystalline metal oxide. In a case where this film is used as a laminate film, processes from coating of a starting material to baking thereof are repeatedly performed. Thereafter, pre-annealing is performed.

As illustrated in FIG. 11, an upper metal film 38 is provided. In the present embodiment, for example, the upper metal film 38 is formed by laminating an iridium film, a titanium film, and an iridium film in this order. A method of providing the upper metal film 38 is not particularly limited, but, in the present embodiment, for example, a sputtering method is used.

As illustrated in FIG. 12, the pyroelectric body material layer 37 and the upper metal film 38 are patterned. A film made of a material of a mask film is provided on the upper metal film 38. The film made of the material of the mask film is exposed and developed by using a photolithography method so as to be patterned, and thus the mask film is formed. Specifically, first, a photosensitive resist film is provided, and a mask having shapes of the piezoelectric body 14 and the piezoelectric body 17 is overlapped thereon so as to be exposed to light. Next, the resist film is removed through etching, and a mask film is provided. A shape of the mask film is a shape of each of the piezoelectric body 14 and the piezoelectric body 17.

A part of the pyroelectric body material layer 37 is removed according to a dry etching method using the mask film as a mask. The pyroelectric body material layer 37 and the upper metal film 38 are etched to be formed in a rectangular shape through the dry etching. Next, the mask film is peeled off by using a peeling liquid.

The upper metal film 38 is patterned. A film made of a material of a mask film is provided on the upper metal film 38. The film made of the material of the mask film is exposed and developed by using a photolithography method so as to be patterned, and thus the mask film is formed. Next, the resist film is removed through etching, and a mask film is provided. A shape of the mask film is a shape of each of the first upper electrode 15 and the second upper electrode 18.

A part of the first upper electrode 15 is removed according to a dry etching method using the mask film as a mask. The upper metal film 38 is etched to be formed in the shape of each of the first upper electrode 15 and the second upper electrode 18 through the dry etching. Next, the mask film is peeled off by using a peeling liquid.

As a result, the first lower electrode 13, the piezoelectric body 14, and the first upper electrode 15 are laminated and provided on the insulating film 12. The second lower electrode 16, the piezoelectric body 17, and the second upper electrode 18 are laminated and provided on the insulating film 12.

Figure 13:
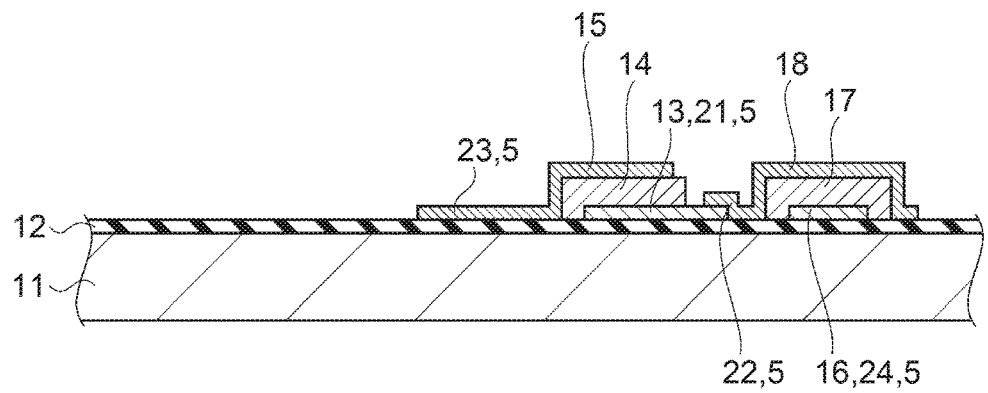
FIG. 13 is a schematic diagram for explaining a manufacturing method of the ultrasonic transducer device.

FIG. 13 is a schematic diagram for explaining a first wire installation process. As illustrated in FIG. 13, the second connection wire 22 and the third connection wire 23 are provided. First, a metal film is formed. The metal film is a material film of the second connection wire 22 and the third connection wire 23. A method of forming the metal film is not particularly limited, but, in the present embodiment, a sputtering method is used.

Next, a film made of a photosensitive material is formed on the metal film. Next, the film is exposed and developed by using a photolithography method so as to be patterned, and thus a mask film is formed. A shape of the mask film is a shape of each of the second connection wire 22 and the third connection wire 23. Next, the metal film is dry-etched by using the mask film as a mask. As a result, the second connection wire 22 and the third connection wire 23 are formed from the metal film. An over-etching amount in a planar direction is smaller in dry etching than in wet etching, and thus a fine pattern can be formed with high accuracy.

Figure 14:
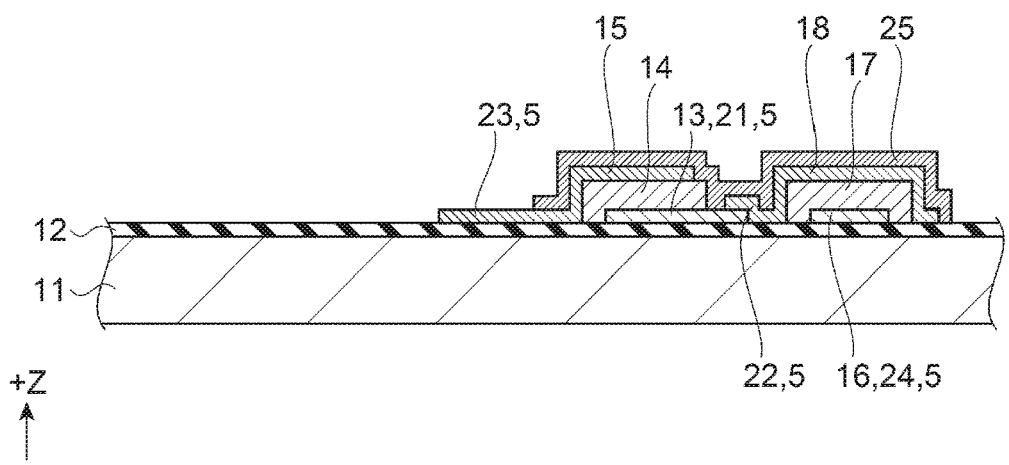
FIG. 14 is a schematic diagram for explaining a manufacturing method of the ultrasonic transducer device.

FIG. 14 is a schematic diagram for explaining a protective film installation process. As illustrated in FIG. 14, the protective film 25 is provided. First, an inorganic film is provided to overlap the first connection wire 21 to the fourth connection wire 24, the piezoelectric body 14, the piezoelectric body 17, the first upper electrode 15, and the second upper electrode 18. The inorganic film is a film of aluminum oxide ($Al_2O_3$), and is formed by using a CVD method. Next, a film made of a photosensitive material is formed. Next, the film is exposed and developed by using a photolithography method so as to be patterned, and thus a mask film is formed. Next, the inorganic film is dry-etched by using the mask film as a mask. As a result, the inorganic film is formed in the shape of the protective film 25.

Next, an organic insulating film is provided to overlap the inorganic film. First, an organic solid film is provided to overlap the inorganic film. The organic solid film is a photosensitive resin film. A solution in which a photosensitive resin material is dissolved is coated on the first substrate 2. A coating method is not particularly limited as long as a predetermined amount of the solution is uniformly coated. In the present embodiment, for example, the solution is coated by using a spin coater. Next, the solution is dried so that a solvent is removed.

Next, the organic solid film is masked in a predetermined pattern and is then exposed to light. The organic solid film is etched to be patterned. As a result, the organic insulating film is provided on the inorganic film, and thus the protective film 25 is completed.

Figure 15:
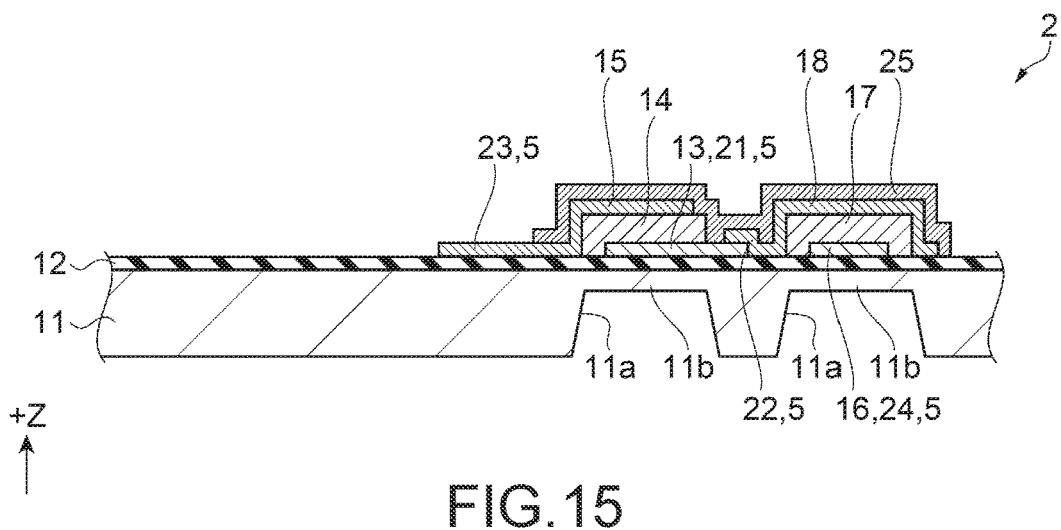
FIG. 15 is a schematic diagram for explaining a manufacturing method of the ultrasonic transducer device.

FIG. 15 is a schematic diagram for explaining a depression installation process. As illustrated in FIG. 15, the first base plate 11 is patterned, and thus the depression 11*a* is provided. Specifically, a film made of a material of a mask film is provided on the surface of the first base plate 11 on the −Z direction side. The film made of the material of the mask film is exposed and developed by using a photolithography method so as to be patterned, and thus the mask film is formed. A shape of the mask film is a planar shape in which the depression 11*a* is open. Next, the first base plate 11 is etched by using the mask film as a mask. Regarding an etching method, the first base plate 11 is etched by using, for example, wet anisotropy etching, or anisotropy etching using an active gas such as parallel plate reactive ion etching. The vibration plate 11*b* functions as an etching stop layer. Next, the mask film is removed. As a result, the depression 11*a* is formed in the first base plate 11. Through the above-described processes, the first substrate 2 is completed.

Figure 16:
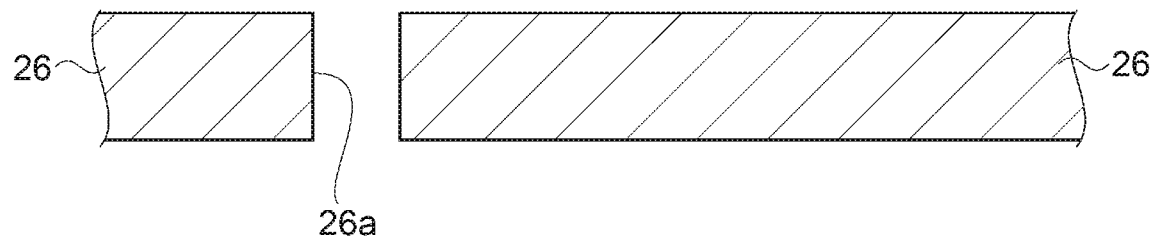
FIG. 16 is a schematic diagram for explaining a manufacturing method of the ultrasonic transducer device.
Figure 17:
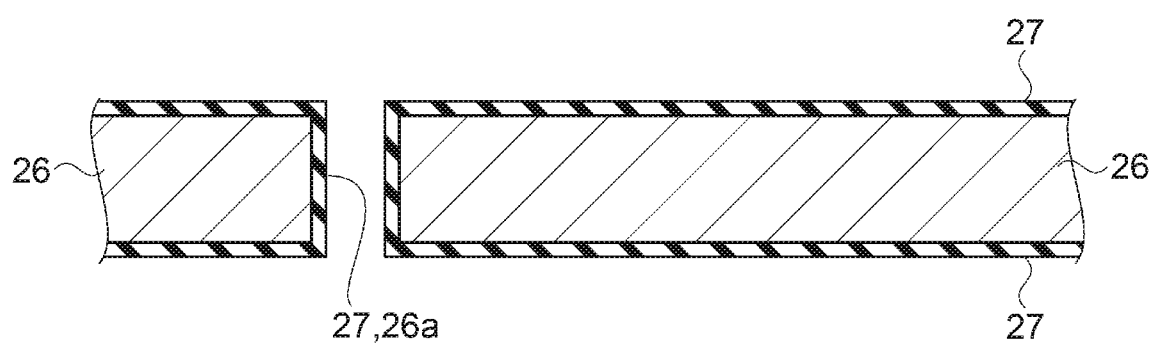
FIG. 17 is a schematic diagram for explaining a manufacturing method of the ultrasonic transducer device.
Figure 18:
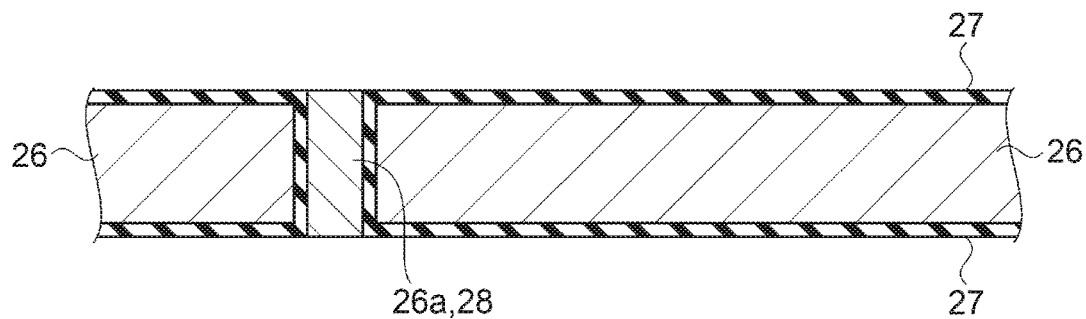
FIG. 18 is a schematic diagram for explaining a manufacturing method of the ultrasonic transducer device.

FIGS. 16 to 18 are schematic diagrams for explaining a through electrode installation process. As illustrated in FIG. 16, the second base plate 26 is prepared. The second base plate 26 is patterned, and thus the through hole 26*a* is provided. A film made of a material of a mask film is provided on surfaces of the second base plate 26 on the +Z direction side and the −Z direction side. The film made of the material of the mask film is exposed and developed by using a photolithography method so as to be patterned, and thus the mask film is formed. A shape of the mask film is a planar shape in which the through hole 26*a* is open. Next, the second base plate 26 is etched by using the mask film as a mask. Regarding an etching method, the second base plate 26 is etched by using, for example, wet anisotropy etching, or anisotropy etching using an active gas such as parallel plate reactive ion etching. Next, the mask film is removed. As a result, the through hole 26*a* is formed in the second base plate 26.

As illustrated in FIG. 17, next, the insulating film 27 is provided on a surface of the second base plate 26. The insulating film 27 is formed by heating the second base plate 26 in an oxygen atmosphere so that silicon is converted into silicon oxide. The insulating film 27 may be formed by laminating silicon dioxide or aluminum oxide. A sputtering method or a CVD method may be used as a method of laminating a material of the insulating film 27.

As illustrated in FIG. 18, next, a metal is provided in the through hole 26*a*, and thus the through electrode 28 is formed. The through electrode 28 is an aluminum alloy film having a film thickness of about 500 nm. The through electrode 28 is formed by using a sputtering method or deposition, and is patterned by using a wet etching method.

Figure 19:
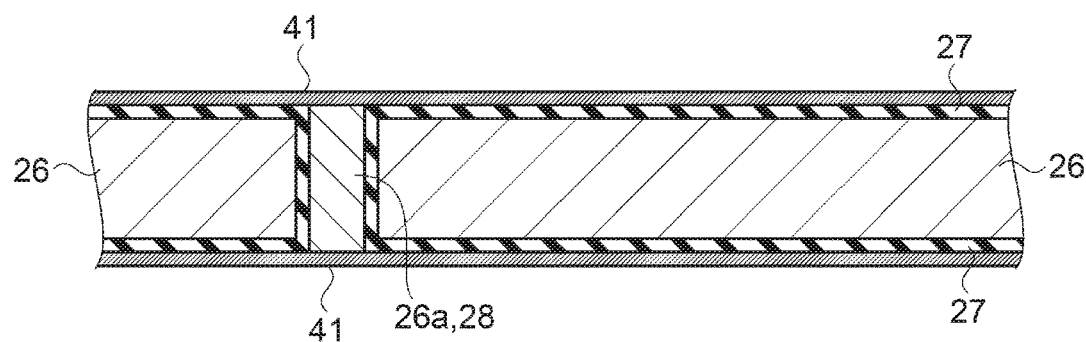
FIG. 19 is a schematic diagram for explaining a manufacturing method of the ultrasonic transducer device.
Figure 20:
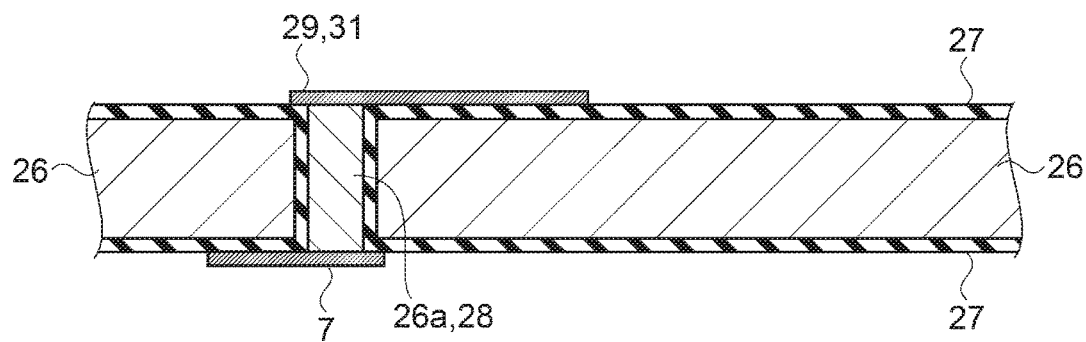
FIG. 20 is a schematic diagram for explaining a manufacturing method of the ultrasonic transducer device.
Figure 21:
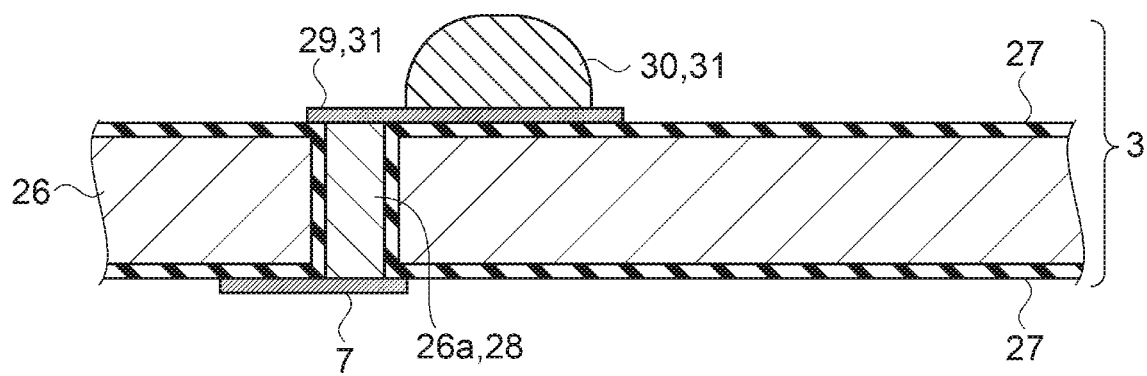
FIG. 21 is a schematic diagram for explaining a manufacturing method of the ultrasonic transducer device.

FIGS. 19 to 21 are schematic diagrams for explaining a second wire installation process. As illustrated in FIG. 19, a metal film 41 is provided on the insulating film 27 on both surfaces of the second base plate 26. A material of the metal film 41 is not particularly limited, and a metal such as gold, silver, copper, or aluminum, or an alloy containing the metal may be used. A sputtering method or a CVD method may be used as a method of providing the metal film 41.

As illustrated in FIG. 20, the metal film 41 is patterned so that the second wire 7 and the fifth connection wire 29 are formed. Specifically, a film made of a photosensitive material is formed on the metal film 41 on both surfaces. Next, the film is exposed and developed by using a photolithography method so as to be patterned, and thus a mask film is formed. A shape of the mask film on one surface is a shape of the second wire 7, and a shape of the mask film on the other surface is a shape of the fifth connection wire 29. Next, the metal film is dry-etched by using the mask film as a mask. As a result, the second wire 7 and the fifth connection wire 29 are formed from the metal film 41.

As illustrated in FIG. 21, the protrusion 30 is provided on the fifth connection wire 29. First, a paste containing a metal serving as a material of the protrusion 30 is disposed on the fifth connection wire 29. Various printing methods may be used as a method of coating the paste. Next, the paste is heated to be melted. The paste contains metal particles and a binder. The binder sublimes through heating, and thus a metal remains on the fifth connection wire 29. The metal is in a liquid state through heating, and has a hemispherical shape due to action of surface tension. The metal is melted and is then cooled so as to be solidified in the hemispherical shape and thus to become the protrusion 30. A method of heating the paste is not particularly limited, and, for example, a method of heating the paste through irradiation with laser light or a method of applying hot air thereto may be used. Through the above-described processes, the second substrate 3 is completed.

Figure 22:
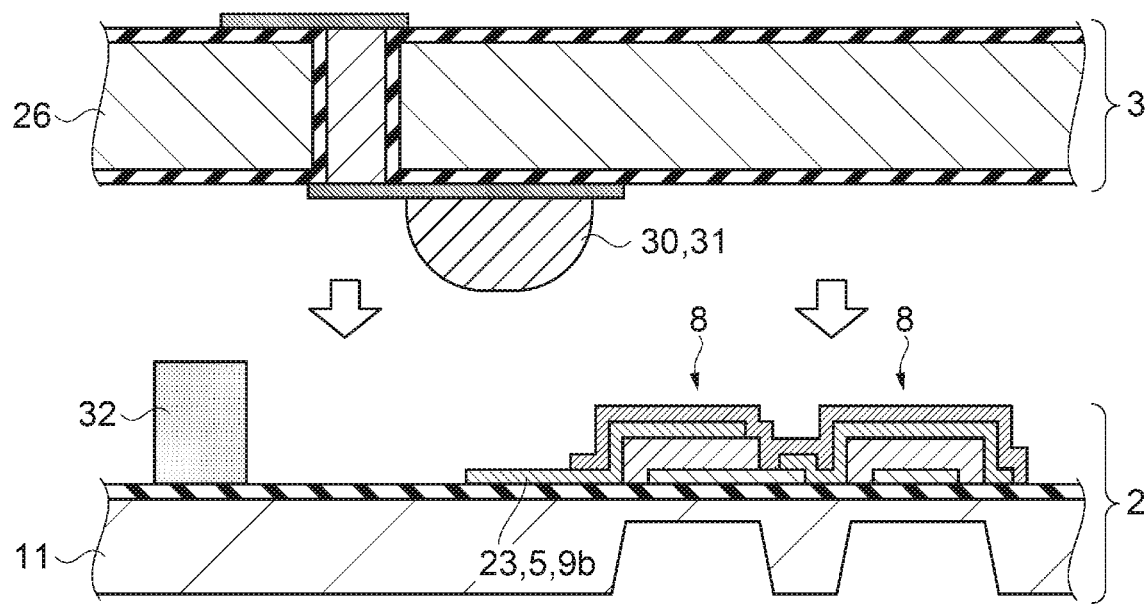
FIG. 22 is a schematic diagram for explaining a manufacturing method of the ultrasonic transducer device.
Figure 23:
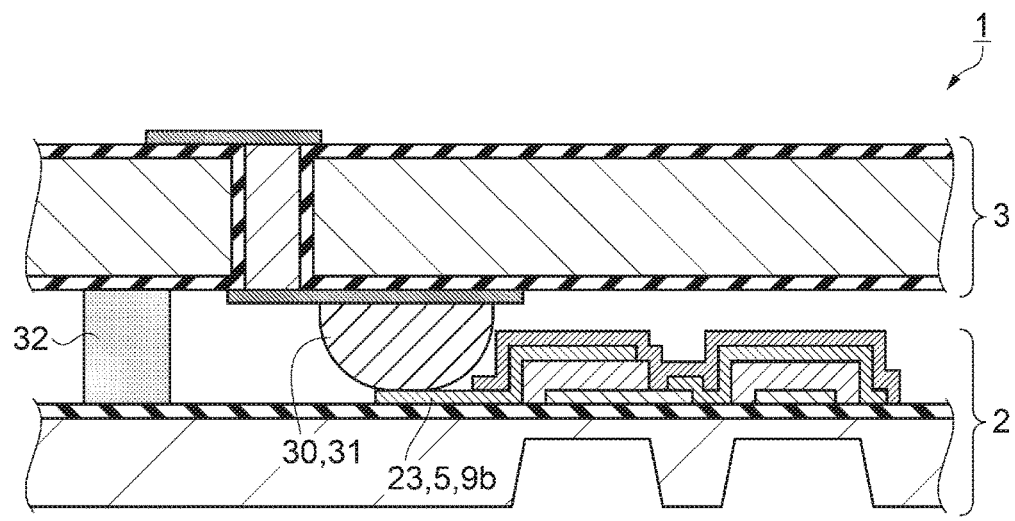
FIG. 23 is a schematic diagram for explaining a manufacturing method of the ultrasonic transducer device.

FIGS. 22 and 23 are schematic diagrams for explaining an assembly process. As illustrated in FIG. 22, the adhesive portion 32 is provided in a distribution manner on the first substrate 2. The adhesive portion 32 may be disposed along an outer periphery of the second substrate 3. A gap between the first substrate 2 and the second substrate 3 is sealed, and thus it is possible to prevent wires from being short-circuited to each other due to permeation of liquids between the first substrate 2 and the second substrate 3. The adhesive portion 32 employs an adhesive which contracts due to heating. Various printing methods may be used as a method of providing an adhesive which is a material of the adhesive portion 32.

Next, the surface of the second substrate 3 on which the protrusion 30 is provided is directed toward the first substrate 2, and the first substrate 2 and the second substrate 3 are aligned. At this time, planar positions are aligned with each other with high accuracy so that the protrusion 30 is brought into contact with the third connection wire 23. The first substrate 2 and the second substrate 3 are adhered to each other through heating. Through the above-described processes, the ultrasonic transducer device 1 illustrated in FIG. 23 is completed.

As described above, according to the present embodiment, the following effects are achieved.

(1) According to the present embodiment, the ultrasonic transducer device 1 includes the first substrate 2 and the second substrate 3. The first substrate 2 and the second substrate 3 are provided to overlap each other. A plurality of ultrasonic elements 8 are arranged in a matrix on the first substrate 2. The ultrasonic elements 8 are electrically connected in series to each other via the first wire 5, and the first wire 5 is provided in a plurality.

A plurality of second wires 7 and third wires 31 are provided on the second substrate 3. The second wire 7 intersects the first wire 5 in a plan view from the thickness direction of the first substrate 2. The first wire 5 is electrically connected to the second wire 7 via the third wire 31.

The ultrasonic element 8 receives the reflected wave 34 so as to output a voltage signal. The ultrasonic element 8 functions as an electric capacitor having a pair of electrodes, and electric charge is accumulated in each electrode when receiving the reflected wave 34. The ultrasonic elements 8 are connected in series to each other, and thus electrostatic capacitance can be reduced. The electrostatic capacitance and the ultrasonic transducer device have an inverse proportion relationship. The ultrasonic elements 8 connected in series can output a change in electric charge in each electrode as a great voltage change by reducing the electrostatic capacitance.

In a case where a plurality of ultrasonic elements 8 connected in series are set as a single ultrasonic element unit 9, the ultrasonic element unit 9 has two terminals. One of the two terminals is referred to as the first terminal 9a, and the other terminal is referred to as the second terminal 9b. The first terminal 9a is connected to the first wire 5, and signals are input and output via the first wire 5. An electrical signal output from the second terminal 9b is output via the first wire 5, the third wire 31, and the second wire 7.

Since a plurality of first wires 5 and a plurality of second wires 7 intersect each other, a direction in which the first wires 5 are arranged and a direction in which the second wires 7 are arranged are different directions. The first wire 5 is connected to the first external terminal 4, and the second wire 7 is connected to the second external terminal 6. The first external terminal 4 and the second external terminal 6 are provided on different sides of the ultrasonic transducer device 1. The first external terminals 4 electrically connected to the first terminals 9a are gathered on one side, and the second external terminals 6 electrically connected to the second terminals 9b are also gathered on another side.

If the number of ultrasonic elements 8 is increased, output terminals being disposed on a plurality of sides can increase a spatial cycle of the terminals more than in a case where the output terminals are disposed on a single side. Wires can be easily provided. Therefore, electrical signals can be easily transmitted from the first wire 5 and the second wire 7 to the first terminal 9a and the second terminal 9b of each ultrasonic element unit 9.

The first wire 5 and the second wire 7 are provided on the different substrates so as to be insulated from each other, and are thus connected to each other at a specific location via the third wire 31. Therefore, it is also possible to prevent an electrical signal from leaking between the first wire 5 and the second wire 7 at even a location where the first wire 5 intersects the second wire 7. As a result, the ultrasonic transducer device 1 can output electrical signals with high sensitivity, and thus the electrical signals can be transmitted from the first wires 5 and the second wires 7 arranged in different directions.

(2) According to the present embodiment, the third wire 31 includes the through electrode 28 and the conductive protrusion 30. The through electrode 28 penetrates through the second substrate 3 so as to be connected to the second wire 7. The through electrode 28 is connected to the first wire 5 via the conductive protrusion 30. Therefore, the first wire 5 and the second wire 7 can be reliably connected to each other via the third wire 31.

(3) According to the present embodiment, the number of ultrasonic elements 8 electrically connected in series is two or more and five or less. If the number of ultrasonic elements 8 is five or less, the sensitivity of the ultrasonic transducer device 1 can be efficiently made favorable. In a case where six or more ultrasonic elements 8 are connected in series to each other, a voltage applied to the ultrasonic element unit 9 is heightened. Since a breakdown voltage of a drive circuit for driving the ultrasonic element unit 9 is required to be heightened, it is difficult to obtain an element forming the drive circuit. Therefore, if the number of ultrasonic elements 8 is five or less, a breakdown voltage of the drive circuit can be lowered, and thus it is possible to easily manufacture the drive circuit.

(4) According to the present embodiment, the ultrasonic transducer device 1 includes the ultrasonic element group 10. The ultrasonic element group 10 includes the ultrasonic element units 9 in each of which a plurality of ultrasonic elements 8 are connected in series to each other and which are arranged in a matrix. The ultrasonic element 8 is a two-terminal element, and the ultrasonic element unit 9 in which the ultrasonic elements 8 are connected in series to each other is a two-terminal unit. One of two terminals is the first terminal 9a, and the other terminal is the second terminal 9b. The first terminal 9a is connected to the first wire 5, and the first wire 5 extends in the first direction 1a. The second terminal 9b is connected to the second wire 7, and the second wire 7 extends in the second direction 1b. The ultrasonic element units 9 are arranged in a matrix, and a plurality of first wires 5 and second wires 7 are provided. The first wires 5 and the second wires 7 intersect each other, and thus a direction in which the first wires 5 are arranged and a direction in which the second wires 7 are arranged are different from each other.

The ultrasonic element 8 receives the reflected wave 34 so as to output a voltage signal. The ultrasonic element 8 functions as an electric capacitor having a pair of electrodes, and electric charge is accumulated in each electrode when receiving the reflected wave 34. The ultrasonic elements 8 are connected in series to each other, and thus electrostatic capacitance can be reduced. The electrostatic capacitance and a voltage output from the ultrasonic element 8 have an inverse proportion relationship. The ultrasonic elements 8 connected in series can output a change in electric charge in each electrode as a great voltage change by reducing the electrostatic capacitance.

The ultrasonic element unit 9 has the first terminal 9a and the second terminal 9b. The first terminal 9a is connected to the first wire 5, and signals are input and output via the first wire 5. The second terminal 9b is connected to the second wire 7, and signals are input and output via the second wire 7. The second direction 1b in which the first wires 5 are arranged and the first direction 1a in which the second wires 7 are arranged are different directions. If the number of ultrasonic elements 8 is increased, output terminals being disposed on a plurality of sides can increase a spatial cycle of the terminals more than in a case where the output terminals are disposed on a single side. Wires can be easily provided.

Therefore, electrical signals can be more easily transmitted to the first terminal 9a and the second terminal 9b of each ultrasonic element unit 9 than in a case where the first wires 5 and the second wires 7 are arranged in the same direction. As a result, the ultrasonic transducer device 1 can output electrical signals with high sensitivity, and can thus transmit the electrical signals from the wires arranged in the different directions.

Second Embodiment

Next, a description will be made of an embodiment of an ultrasonic transducer device with reference to FIG. 24 which is a main portion schematic side sectional view illustrating a configuration of an ultrasonic transducer device. A difference between the present embodiment and the first embodiment is that a through hole is provided at a location facing the ultrasonic element 8 in the second substrate 3. The same content as that in the first embodiment will not be described.

Figure 24:
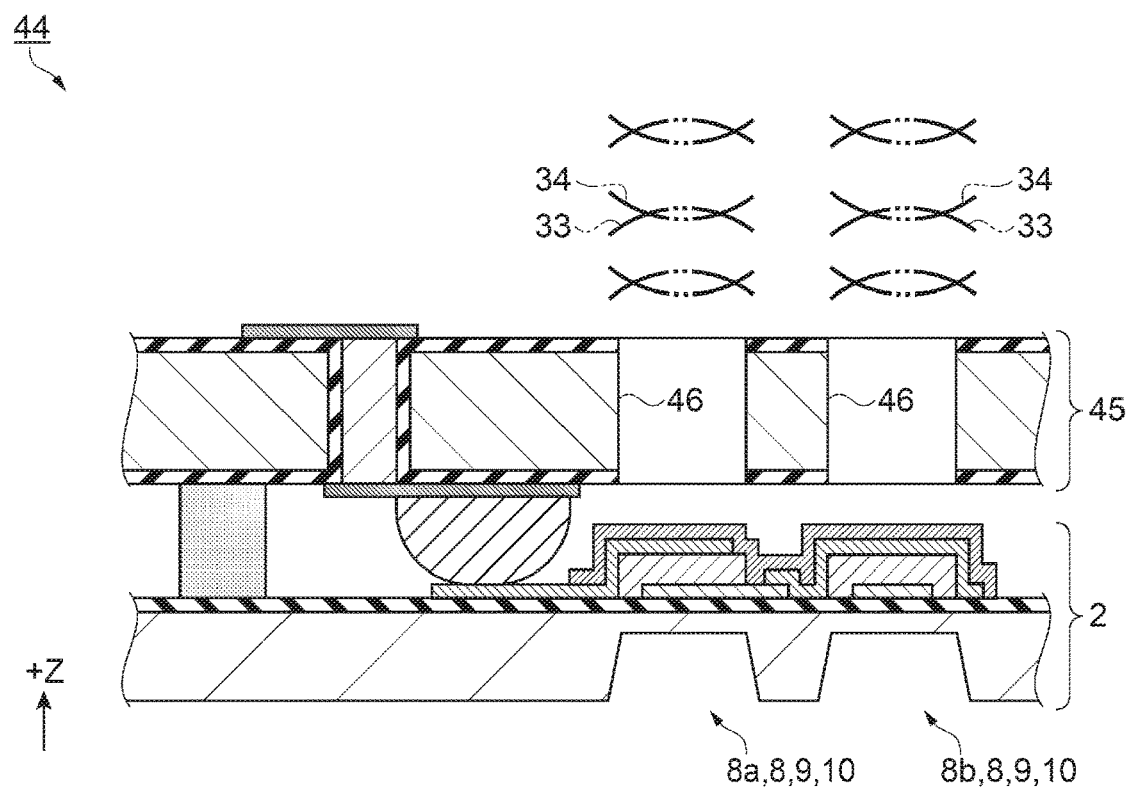
FIG. 24 is a main portion schematic side sectional view illustrating a configuration of an ultrasonic transducer device according to a second embodiment.

In other words, in the present embodiment, as illustrated in FIG. 24, an ultrasonic transducer device 44, the first substrate 2 is provided to overlap a second substrate 45. A through hole 46 is provided at a location facing the ultrasonic element 8 in the second substrate 45. The ultrasonic wave 33 which is emitted from the ultrasonic element 8 in the +Z direction can be caused to advance in the +Z direction through the through hole 46.

The reflected wave 34 which advances toward the ultrasonic element 8 from the +Z direction side passes through the through hole 46. The ultrasonic element 8 can receive the reflected wave 34. Therefore, the ultrasonic wave 33 can be emitted toward a subject located on the second substrate 45 side and can receive the reflected wave 34.

Third Embodiment

Figure 25:
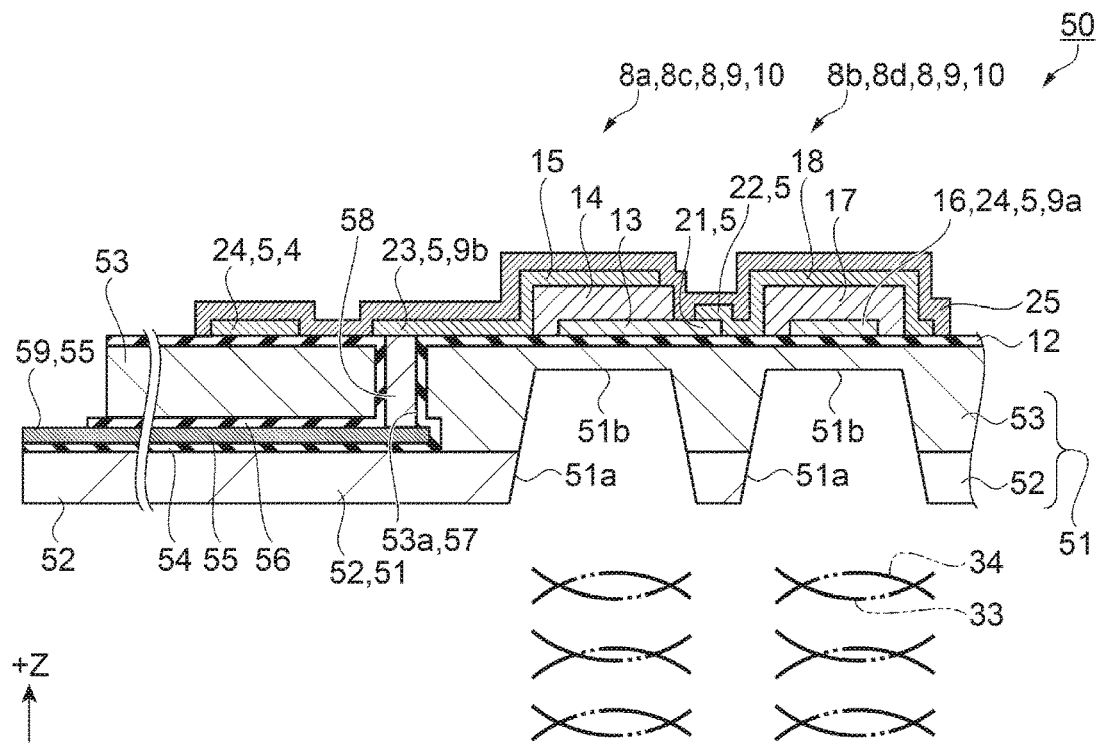
FIG. 25 is a main portion schematic side sectional view illustrating a configuration of an ultrasonic transducer device according to a third embodiment.
Figure 26:
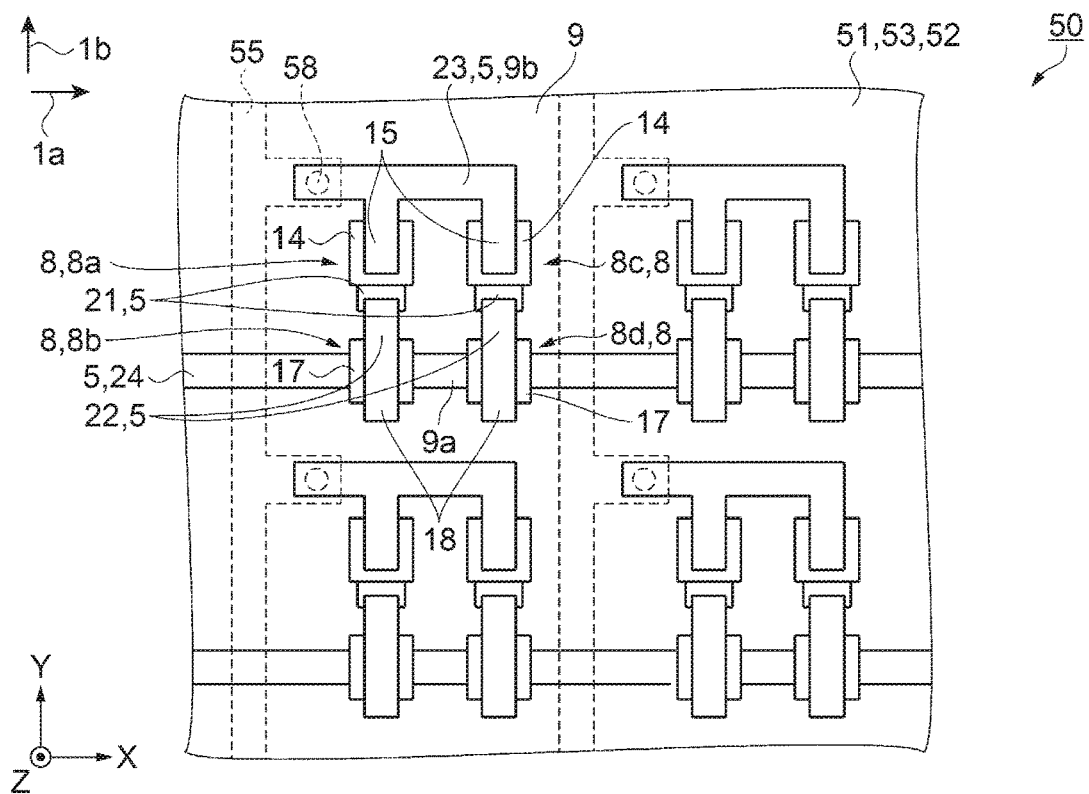
FIG. 26 is a main portion schematic plan view illustrating a configuration of the ultrasonic transducer device.

Next, a description will be made of an embodiment of an ultrasonic transducer device with reference to FIGS. 25 and 26. FIG. 25 is a main portion schematic side sectional view illustrating a configuration of an ultrasonic transducer device. FIG. 26 is a main portion schematic plan view illustrating a configuration of the ultrasonic transducer device. A difference between the present embodiment and the first embodiment is that a wire corresponding to the second wire 7 is provided inside the first base plate 11. The same content as that in the first embodiment will not be described.

In other words, in the present embodiment, as illustrated in FIG. 25, an ultrasonic transducer device 50 includes a base substrate 51. The ultrasonic elements 8 forming the ultrasonic element unit 9 are provided to be arranged on the base substrate 51. The ultrasonic elements 8 on the left in the figure are respectively the first element 8a and the third element 8c, and the ultrasonic elements 8 on the right in the figure are respectively the second element 8b and the fourth element 8d.

The base substrate 51 includes a low substrate 52 and an upper substrate 53 which are provided to overlap each other as substrates. A depression 51a is provided at a location facing the ultrasonic element 8 in the base substrate 51. A thickness of the base substrate 51 is small in the depression 51a. The thin portion of the base substrate 51 is a vibration plate 51b which easily vibrates.

The same silicon as that of the first base plate 11 in the first embodiment is used as a material of the low substrate 52 and the upper substrate 53. The same silicon dioxide or zirconium dioxide as that of the vibration plate 11b in the first embodiment is used as a material of the vibration plate 51b.

The insulating film 12 is provided on the +Z direction side of the base substrate 51. The ultrasonic elements 8 including the first element 8a to the fourth element 8d are provided on the insulating film 12. A plurality of ultrasonic elements 8 are provided on the insulating film 12 and are arranged in a matrix. A structure of each of the first element 8a to the fourth element 8d is the same as that in the first embodiment. The fourth connection wire 24 connected to the second lower electrode 16 is provided on the insulating film 12. The protective film 25 covering the ultrasonic element 8 covers both of the third connection wire 23 and the fourth connection wire 24.

The first connection wire 21, the second connection wire 22, the third connection wire 23, and the fourth connection wire 24 are wires via which the first elements 8a and the second elements 8b are electrically connected in series to each other, and are wires forming the first wire 5. A plurality of first wires 5 are provided on the insulating film 12.

An insulating film 54 is provided on the low substrate 52, and the insulating film 54 covers a part of the surface of the low substrate 52 on the +Z direction side. A plurality of second wires 55 are provided on the insulating film 54. In other words, the plurality of second wires 55 are provided on the low substrate 52 via the insulating film 54. The second wire 55 is a wire corresponding to the second wire 7 in the first embodiment.

An insulating film 56 is provided to overlap the second wire 55. The upper substrate 53 is provided to overlap the insulating film 56, and the insulating film 12 is provided on the upper substrate 53. Therefore, the insulating film 12 is provided to overlap the second wire 55 via the insulating film 56 and the upper substrate 53. The second wire 55 is surrounded by the insulating film 54 and the insulating film 56. Therefore, a current does not leak from the second wire 55 to the low substrate 52 or the upper substrate 53.

A through hole 53a is provided between the third connection wire 23 and the second wire 55 in the upper substrate 53. An insulating film 57 is provided on an inner circumference of the through hole 53a. A through electrode 58 as the third wire is provided inside the insulating film 57. The third connection wire 23 and the second wire 55 are electrically connected to each other via the through electrode 58. The third connection wire 23 is a part of the first wire 5, and thus the first wire 5 and the second wire 55 are electrically connected to each other via the through electrode 58.

The second wire 55 is exposed at an end of the low substrate 52 on the left in the figure so as to serve as a second external terminal 59. The first wire 5 is connected to the first external terminal 4. A voltage waveform is applied between the first external terminal 4 and the second external terminal 59, and thus the ultrasonic element 8 emits the ultrasonic wave 33. The ultrasonic element 8 converts the received reflected wave 34 into an electrical signal. The ultrasonic element 8 outputs the converted electrical signal from the first external terminal 4 and the second external terminal 59.

A silicon substrate may be used as the upper substrate 53, and a silicon layer may be formed on the low substrate 52. In a case where the silicon substrate is used as the upper substrate 53, the insulating film 54, the second wire 55, and the insulating film 56 are provided on the low substrate 52. The insulating film 57 and the through electrode 58 are provided on the upper substrate 53. The low substrate 52 is bonded to the upper substrate 53 so that the base substrate 51 is formed. In a case where a silicon layer is used for the upper substrate 53, the upper substrate 53 is formed by using a sputtering method or a CVD method. The through hole 53a is provided in the upper substrate 53, and the insulating film 57 and the through electrode 58 are provided in the through hole 53a.

As illustrated in FIG. 26, a plurality of second wires 55 are provided on the low substrate 52, and a plurality of first wires 5 are provided on the upper substrate 53. The first wires 5 extend in the first direction 1a, and are arranged side by side in the second direction 1b. The second wires 55 extend in the second direction 1b, and are arranged side by side in the first direction 1a. The plurality of second wires 55 intersect the plurality of first wires 5 in a plan view from the thickness direction of the low substrate 52.

As described above, according to the present embodiment, the following effects are achieved.

(1) According to the present embodiment, the ultrasonic transducer device 50 includes the low substrate 52, and the second wire 55 is provided on the low substrate 52. The insulating film 12 is provided to overlap the second wire 55. A plurality of ultrasonic elements 8 are provided on the insulating film 12, and the ultrasonic elements 8 are arranged in a matrix. The ultrasonic elements 8 are electrically connected to each other as a plurality of serial sets via the first wires 5. The second wire 55 intersects the first wire 5 in a plan view from the thickness direction of the low substrate 52. The first wire 5 and the second wire 55 are provided in a plurality. The first wire 5 is electrically connected to the second wire 55 via the through electrode 58.

The ultrasonic element 8 receives the reflected wave 34 and outputs a voltage signal. The ultrasonic element 8 functions as an electric capacitor having a pair of electrodes, and electric charge is accumulated in each electrode when receiving the reflected wave 34. The ultrasonic elements 8 are connected in series to each other, and thus electrostatic capacitance can be reduced. The electrostatic capacitance and the ultrasonic element 8 have an inverse proportion relationship. The ultrasonic elements 8 connected in series can output a change in electric charge in each electrode as a great voltage change by reducing the electrostatic capacitance.

In a case where a plurality of ultrasonic elements 8 connected in series are set as a single ultrasonic element unit 9, the ultrasonic element unit 9 has two terminals. One of the two terminals is the first terminal 9a, and the other terminal is the second terminal 9b. The first terminal 9a is connected to the first wire 5, and electrical signals are input and output via the first wire 5. An electrical signal output from the second terminal 9b is output via the first wire 5, the through electrode 58, and the second wire 55. Since a plurality of first wires 5 and a plurality of second wires 55 intersect each other, the second direction 1b in which the first wires 5 are arranged and the first direction 1a in which the second wires 55 are arranged are different directions. Therefore, electrical signals can be easily transmitted to the first terminal 9a and the second terminal 9b of each ultrasonic element unit 9.

The first wire 5 and the second wire 55 are provided with the insulating film 12 interposed therebetween so as to be insulated from each other, and are thus connected to each other at only a specific location via the through electrode 58. Therefore, it is also possible to prevent an electrical signal from leaking between the first wire 5 and the second wire 55 even at a location where the first wire 5 intersects the second wire 55. As a result, the ultrasonic element 8 can output electrical signals with high sensitivity, and thus the electrical signals can be transmitted from the wires arranged in different directions.

Fourth Embodiment

Next, a description will be made of an embodiment of an ultrasonic apparatus including an ultrasonic probe mounted with the ultrasonic transducer device with reference to FIG. 27 which is a schematic perspective view illustrating a configuration of the ultrasonic apparatus. An ultrasonic transducer device mounted on the ultrasonic probe and the ultrasonic apparatus in the present embodiment is the ultrasonic transducer device described in the first to third embodiments. The same content as that in the first to third embodiments will not be described.

Figure 27:
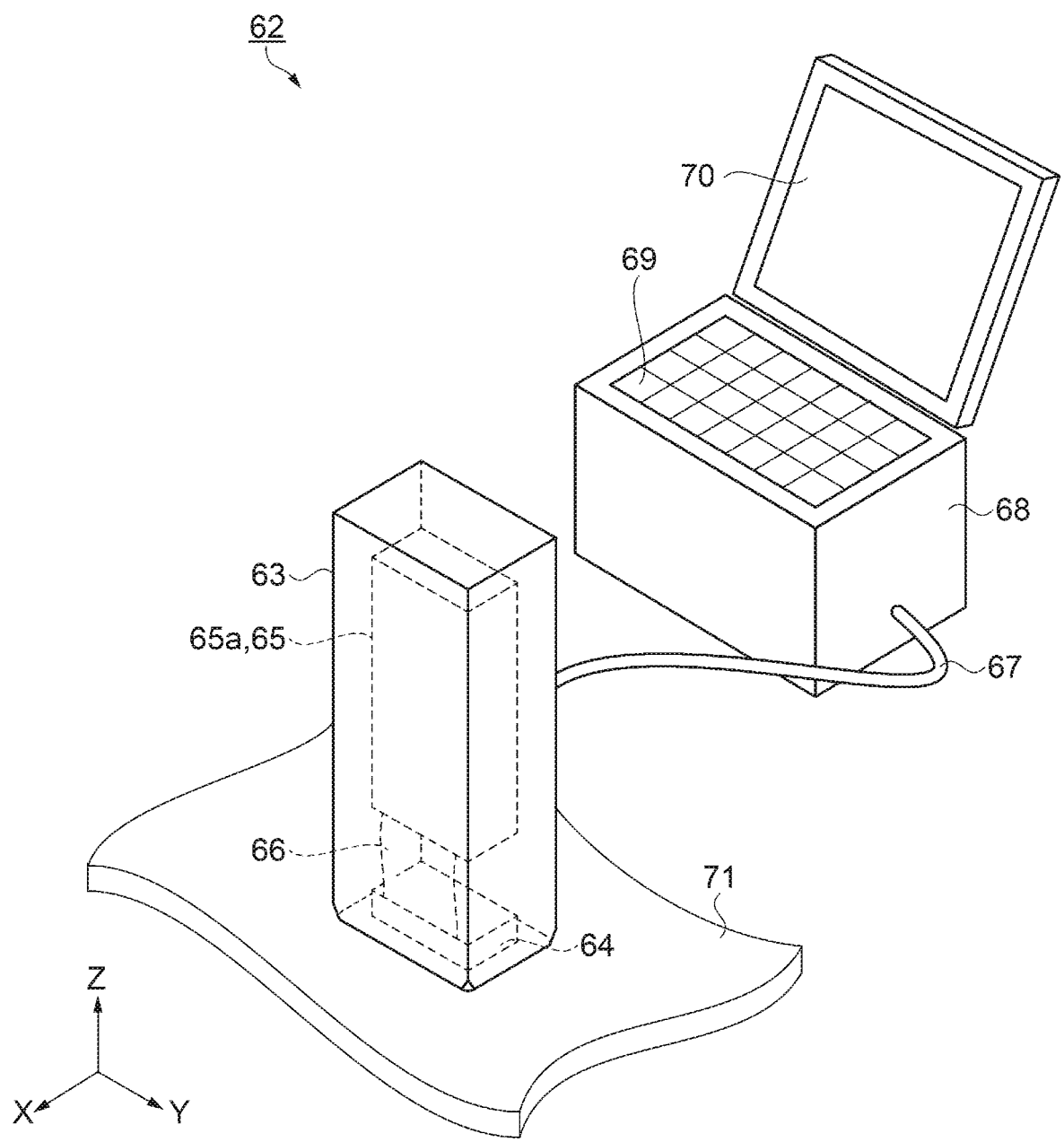
FIG. 27 is a schematic perspective view illustrating a configuration of an ultrasonic apparatus according to a fourth embodiment.

As illustrated in FIG. 27, an ultrasonic apparatus 62 includes an ultrasonic probe 63. The ultrasonic probe 63 substantially has a rectangular parallelepiped shape which is long in one direction, and is thus for an operator to easily hold. A longitudinal direction of the ultrasonic probe 63 is set as the Z direction. A surface of the ultrasonic probe 63 on the −Z direction is a substantially flat surface, and a planar shape thereof is a rectangular shape. Directions in which two sides of the planar shape which are orthogonal to each other extend are respectively set as the X direction and the Y direction.

An ultrasonic transducer device 64 is provided on the −Z direction side of the ultrasonic probe 63. The ultrasonic transducer device 64 receives the reflected wave 34 and outputs an electrical signal. Anyone of the ultrasonic transducer device 1, the ultrasonic transducer device 44, and the ultrasonic transducer device 50 described above is used as the ultrasonic transducer device 64.

The ultrasonic transducer device 64 is exposed from a casing on the surface of the ultrasonic probe 63 on the −Z direction side. The ultrasonic probe 63 includes a controller 65 controlling the ultrasonic transducer device 64 therein, and the ultrasonic transducer device 64 is connected to the controller 65 via a cable 66. The controller 65 includes a central processing unit (CPU) and a storage device. The storage device stores data regarding drive waveforms for driving the ultrasonic transducer device 64, or a program regarding procedures for driving the ultrasonic transducer device 64. The CPU outputs drive waveforms to the ultrasonic transducer device 64 according to the program, so as to drive the ultrasonic transducer device 64.

The ultrasonic probe 63 is connected to a control device 68 via a cable 67. The control device 68 is a device which receives a data signal output from the ultrasonic probe 63, and analyzes and displays the data signal. The control device 68 also includes a CPU and a storage device. The CPU performs various calculations or control according to a program. The control device 68 is provided with an input device 69 and a display 70. The input device 69 is a device such as pointing devices including a keyboard, a mouse pad, a dedicated switch, and a track ball, and is a device which is used for an operator to input the instruction content to the control device 68. The display 70 is not particularly limited as long as a data signal can be generated and displayed as an image, and a liquid crystal display or an organic light emitting diode (OLED) display device may be used. In the present embodiment, for example, an OLED display device is used as the display 70.

The ultrasonic probe 63 is used in a state of being pressed against a surface of a subject 71. The ultrasonic probe 63 emits the ultrasonic wave 33 from the ultrasonic transducer device 64 toward the subject 71. The ultrasonic transducer device 64 emits the ultrasonic wave 33 to the subject 71, and receives the reflected wave 34 which is reflected from the inside of the subject 71. The ultrasonic transducer device 64 receives the reflected wave 34 so as to output an electrical signal. Since a time difference in reflection and returning between the reflected waves 34 occurs due to reflection surfaces, nondestructive inspection of an internal structure of the subject 71 can be performed by analyzing the time taken for the reflected wave 34 to return.

The signal corresponding to the reflected wave received by the ultrasonic transducer device 64 is output to the controller 65. The controller 65 includes a converter 65*a* which performs analog-to-digital (A/D) conversion, and the converter 65*a* converts the electrical signal output from the ultrasonic transducer device 64 into a data signal with a digital format. The data signal with a digital format is transmitted to the control device 68 from the controller 65 via the cable 67. The control device 68 receives and analyzes the data signal corresponding to the reflected wave. The control device 68 converts the data signal corresponding to the reflected wave into an image representing an internal structure of the subject 71, and the display 70 displays the image into which the data signal corresponding to the reflected wave is converted.

As described above, according to the present embodiment, the following effects are achieved.

(1) According to the present embodiment, the ultrasonic probe 63 includes the ultrasonic transducer device 64 which receives the reflected wave 34 so as to output an electrical signal. The ultrasonic transducer device 64 is any one of the ultrasonic transducer device 1, the ultrasonic transducer device 44, and the ultrasonic transducer device 50 described above. The ultrasonic transducer device 1, the ultrasonic transducer device 44, or the ultrasonic transducer device 50 described above can output electrical signals with high sensitivity, and can transmit the electrical signals from the wires arranged in different directions. Therefore, the ultrasonic probe 63 can acquire the signals with high sensitivity, and can thus be implemented as a device including the ultrasonic transducer device 64 which can transmit electrical signals from the wires arranged in different directions.

(2) According to the present embodiment, the ultrasonic apparatus 62 includes the ultrasonic transducer device 64, the converter 65*a*, and the display 70. The ultrasonic transducer device 64 receives the reflected wave 34 so as to output an electrical signal. The converter 65*a* converts the electrical signal into a data signal. The display 70 displays the data signal. Any one of the ultrasonic transducer device 1, the ultrasonic transducer device 44, and the ultrasonic transducer device 50 described above is used as the ultrasonic transducer device 64. The ultrasonic transducer device 1, the ultrasonic transducer device 44, or the ultrasonic transducer device 50 described above can output electrical signals with high sensitivity, and can transmit the electrical signals from the wires arranged in different directions. Therefore, the ultrasonic apparatus 62 can output the electrical signals with high sensitivity, and can thus be implemented as an apparatus including the ultrasonic transducer device 64 which can transmit electrical signals from the wires arranged in different directions.

The present embodiment is not limited to the above-described embodiment, and may be variously modified or altered within the technical spirit of the invention by a person skilled in the art. Modification examples will be described below.

Modification Example 1

In the first embodiment, the ultrasonic element unit 9 has a configuration in which two sets of the ultrasonic elements 8 connected in series are connected in parallel to each other. The ultrasonic element unit 9 may have a configuration in which a single set of the ultrasonic elements 8 connected in series may be used, or three or more sets of ultrasonic elements 8 connected in series may be connected in parallel to each other. If the number of sets connected in parallel is small, an ultrasonic image having a high spatial resolution can be obtained. If the number of sets connected in parallel is large, the reflected waves 34 are averaged, and thus an ultrasonic image having less noise can be obtained. A lot of ultrasonic elements 8 output voltage waveforms as a single element, and thus the reflected wave 34 can be received with high sensitivity.

Modification Example 2

In the first embodiment, a metal is used as a material of the protrusion 30. The protrusion 30 may be made of a resin material, and a metal film may be provided on a surface of the protrusion 30. The protrusion 30 is elastic, and thus the reliability of connection can be increased.

The entire disclosure of Japanese Patent Application No. 2016-222948 filed Nov. 16, 2016 is expressly incorporated by reference herein.

What is claimed is:

1. An ultrasonic transducer device comprising:
a first substrate that is provided with a plurality of ultrasonic transducer elements arranged in a matrix, and a plurality of first wires via which the ultrasonic transducer elements are electrically connected to each other as a plurality of serial sets; and
a second substrate that is provided to overlap the first substrate, and is provided with a plurality of second wires intersecting the first wires in a plan view from a thickness direction of the first substrate and third wires via which the first wires are electrically connected to the second wires,
wherein the third wires include:
through electrodes that penetrate through the second substrate in the thickness direction and are connected to the second wires, and
conductive protrusions protruding toward the thickness direction via which the through electrodes are connected to the first wires, and
wherein, for each corresponding through electrode, conductive protrusion, and transducer element, the conductive protrusions are disposed on a side of the through electrodes that is closer to the ultrasonic transducer elements in the thickness direction.

2. The ultrasonic transducer device according to claim 1, wherein the number of ultrasonic transducer elements electrically connected as the serial sets is two or more and five or less.

3. An ultrasonic probe comprising:
an ultrasonic transducer device that receives an ultrasonic wave and outputs an electrical signal,
wherein the ultrasonic transducer device is the ultrasonic transducer device according to claim 2.

4. An ultrasonic apparatus comprising:
an ultrasonic transducer device that receives an ultrasonic wave and outputs an electrical signal;
a converter that converts the electrical signal output from the ultrasonic transducer device into a data signal; and
a display that displays the data signal,
wherein the ultrasonic transducer device is the ultrasonic transducer device according to claim 2.

5. An ultrasonic probe comprising:
an ultrasonic transducer device that receives an ultrasonic wave and outputs an electrical signal,
wherein the ultrasonic transducer device is the ultrasonic transducer device according to claim 1.

6. An ultrasonic apparatus comprising:
an ultrasonic transducer device that receives an ultrasonic wave and outputs an electrical signal;
a converter that converts the electrical signal output from the ultrasonic transducer device into a data signal; and
a display that displays the data signal,
wherein the ultrasonic transducer device is the ultrasonic transducer device according to claim 1.

7. An ultrasonic transducer device comprising:
a substrate;
a plurality of second wires that are provided on the substrate;
an insulating film that is provided to overlap the second wires;
a plurality of ultrasonic transducer elements that are provided on the insulating film and are arranged in a matrix;
a plurality of first wires via which the ultrasonic transducer elements are electrically connected to each other as a plurality of serial sets and that intersect the second wires in a plan view from a thickness direction of the substrate; and
third wires via which the first wires are electrically connected to the second wires,
wherein the third wires include:
through electrodes that penetrate through the substrate in the thickness direction and are connected to the second wires, and
conductive protrusions protruding toward the thickness direction via which the through electrodes are connected to the first wires, and
wherein, for each corresponding through electrode, conductive protrusion, and transducer element, the conductive protrusions are disposed on a side of the through electrodes that is closer to the ultrasonic transducer elements in the thickness direction.

8. The ultrasonic transducer device according to claim 7, wherein the number of ultrasonic transducer elements electrically connected as the serial sets is two or more and five or less.

9. An ultrasonic probe comprising:
an ultrasonic transducer device that receives an ultrasonic wave and outputs an electrical signal,
wherein the ultrasonic transducer device is the ultrasonic transducer device according to claim 8.

10. An ultrasonic apparatus comprising:
an ultrasonic transducer device that receives an ultrasonic wave and outputs an electrical signal;
a converter that converts the electrical signal output from the ultrasonic transducer device into a data signal; and
a display that displays the data signal,
wherein the ultrasonic transducer device is the ultrasonic transducer device according to claim 8.

11. An ultrasonic probe comprising:
an ultrasonic transducer device that receives an ultrasonic wave and outputs an electrical signal,
wherein the ultrasonic transducer device is the ultrasonic transducer device according to claim 7.

12. An ultrasonic apparatus comprising:
an ultrasonic transducer device that receives an ultrasonic wave and outputs an electrical signal;
a converter that converts the electrical signal output from the ultrasonic transducer device into a data signal; and
a display that displays the data signal,
wherein the ultrasonic transducer device is the ultrasonic transducer device according to claim 7.

* * * * *